(12) United States Patent
Reineke et al.

(10) Patent No.: US 11,564,884 B2
(45) Date of Patent: Jan. 31, 2023

(54) CATIONIC BLOCK POLYMER MICELLES FOR DELIVERY OF BIOLOGICAL AGENTS

(71) Applicant: Regents of the University of Minnesota, Minneapolis, MN (US)

(72) Inventors: Theresa Reineke, Vadnais Heights, MN (US); Zhe Tan, Secaucus, NJ (US); Yaming Jiang, Marlborough, MA (US); Mitra S Ganewatta, Ladson, SC (US); Timothy P. Lodge, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 148 days.

(21) Appl. No.: 17/015,968

(22) Filed: Sep. 9, 2020

(65) Prior Publication Data
US 2021/0069111 A1    Mar. 11, 2021

Related U.S. Application Data

(60) Provisional application No. 62/897,660, filed on Sep. 9, 2019.

(51) Int. Cl.
*A61K 9/107* (2006.01)
*A61K 47/10* (2017.01)
(Continued)

(52) U.S. Cl.
CPC .......... *A61K 9/1075* (2013.01); *A61K 47/10* (2013.01); *A61K 47/32* (2013.01); *A61K 9/08* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,916,488 B1 * | 7/2005 | Meier | A61K 9/5146 424/9.51 |
| 9,884,074 B2 | 2/2018 | Cooper et al. | |
| 2015/0024488 A1 | 1/2015 | Gunatillake et al. | |

FOREIGN PATENT DOCUMENTS

| | | |
|---|---|---|
| EP | 2729182 A1 | 5/2014 |
| WO | 2017/192512 A2 | 11/2017 |
| WO | 2018/156617 A2 | 8/2018 |

OTHER PUBLICATIONS

Sharma et al., "Effects of the Incorporation of a Hydrophobic Middle Block into a PEG-Polycation Diblock Copolymer on the Physiochemical and Cell Interaction Properties of the Polymer-DNA Complexes," NIH Public Access, Biomacromolecules, vol. 9, No. 11, doi:10.1021/bm800876v Nov. 2008, pp. 3294-3307.

(Continued)

*Primary Examiner* — Melissa S Mercier
(74) *Attorney, Agent, or Firm* — Shumaker & Sieffert, P.A.

(57) ABSTRACT

A compound includes an amphiphilic polymer with a hydrophobic block including monomeric units chosen from alkyl (meth)acrylates, alkyl (meth)acrylamides, and combinations thereof; and a hydrophilic cationic block including monomeric units chosen from alkylamino (meth)acrylates, alkylamino (meth)acrylamides, and combinations thereof. The polymer is in the form of a micelle with a central core derived from the hydrophobic block and shell at least partially surrounding the core. The shell includes a plurality of filamentous arms derived from the hydrophilic block and emanating outward from the core. A biological agent is associated with the arms of the micelle.

24 Claims, 25 Drawing Sheets

(51) Int. Cl.
    A61K 47/32     (2006.01)
    A61K 9/08      (2006.01)
    A61K 45/06     (2006.01)

(56) References Cited

OTHER PUBLICATIONS

Adolph et al., "Enhanced Performance of Plasmid DNA Polyplexes Stabilized by a Combination of Core Hydrophobicity and Surface PEGylation," NIH Public Access, J Mater Chem B Mater Biol Med., vol. 2, No. 46, doi:10.1039/C4TB00352G, Dec. 14, 2014, pp. 8154-8164.

Foldvari et al., "Non-viral gene therapy: Gains and Challenges of non-invasive administration methods," ELSEVIER, ScienceDirect, Journal of Controlled Release, Dec. 9, 2015, 27 pp.

Boussif et al., "A versatile vector for gene and oligoneucleotide transfer into cells in culture and in vivo: Polyethylenimine," Proceedings of the National Academy of Sciences of the United States of America, Biochemistry, vol. 92, No. 16, Aug. 1995, pp. 7297-7301.

Fichter et al., "Polymeric Nucleic Acid Vehicles Exploit Active Interorganelle Trafficking Mechanisms," American Chemical Society, ACSNANO, vol. 7, No. 1, https://doi.org/10.1021/nn304218q, Dec. 12, 2012, pp. 347-364.

Li et al., "Poly(2-deoxy-2-methacrylamido glucopyranose)-b-Poly(methacrylate amine)s: Optimization of Diblock Glycopolycations for Nucleic Acid Delivery," American Chemical Society, ACS Publications, ACS Macro Letters, vol. 2, No. 3, https://doi.org/10.1021/mz300660t, Feb. 26, 2013, pp. 230-235.

Sprouse et al., "Investigating the Effects of Block versus Statistical Glycopolycations Containing Primary and Tertiary Amines for Plasmid DNA Delivery," American Chemical Society, ACS Publications, BioMacromolecules, vol. 15, No. 7, https://doi.org/10.1021/bm5004527, Jun. 5, 2014, pp. 2616-2628.

Ogris et al., "PEGylated DNA/transferrin-PEI complexes: reduced interaction with blood components, extended circulation in blood and potential for systemic gene delivery," Stockton Press, Gene Therapy, vol. 6, No. 4, https://doi.org/10.1038/sj.gt.3300900, Dec. 21, 1998, pp. 595-605.

Mishra et al., "Reconstitutable Charged Polymeric (PLGA)2-b-PEI Micelles for Gene Therapeutics Delivery," NIH Public Access, Biomaterials, vol. 32, No. 15, https://doi.org/10.1016/j.biomaterials.2011.01.077, May 2011, pp. 3845-3854.

Gary et al., "The Influence of Nano-Carrier Architecture on In Vitro siRNA Delivery Performance and In Vivo Biodistribution: Polyplexes vs. Micelleplexes," NIH Public Access, ACS Nano, vol. 5, No. 5, https://doi.org/10.1021/nn102540y, May 24, 2011, pp. 3493-3505.

"JetPEI—DNA transfection reagent," Polyplus-transfection, accessed from https://www.polyplus-transfection.com/products/jetpei/, accessed on Mar. 3, 2019, 4 pp.

"Therapeutics Page—Discover the Polyplus-transfection product range," Polyplus-transfection, accessed from https://www.polyplus-transfection.com/products/, accessed on Mar. 3, 2019, 6 pp.

Yu et al., "Overcoming Endosomal Barrier by Amphotericin B-Loaded Dual pH-Responsive PDMA-b-PDPA Micelleplexes for siRNA Delivery," HHS Public Access, ACS Nano, vol. 5, No. 11, https://doi.org/10.1021/nn203503h, Nov. 22, 2011, pp. 9246-9255.

Sharma et al., "Effects of the Incorporation of the Hydrophobic Middle Block into a PEG-Polycation Diblock Copolymer on the Physiochecmical and Cell Interaction Properties of the Polymer-DNA Complexes," NIH Public Access, PMC, Biomacrmoledcules, vol. 8, No. 11, doi:10.1021/bm800876v, Nov. 2008, pp. 3294-3307.

Johnson et al., "Impact of Polymer Excipient Molar Mass and End Groups on Hydrophobic Drug Solubility Enhancement," ACS Publications, American Chemical Society, Macromolecules, vol. 50, No. 3, https://doi.org/10.1021/acs.macromol.6b02474, Jan. 2017, pp. 1102-1112.

Li et al., "Maintaining Hydophobic Drug Supersaturation in a Micelle Corona Reservoir," ACS Publications, American Chemical Society, Macromolecules, vol. 51, No. 2, https://doi.org/10.1021/acs.macromol.7b02297, Jan. 2018, pp. 540-551.

Du et al., "Self-assembly of Hydrophilic Homopolymers: A Matter of End Groups?," Wiley Online Library, Materials Science, Small Structures, vol. 7, Issue 14, DOI:10.1002/smll.201100382, June 7, 2011, pp. 2070-2080.

Sprouse et al., "Tuning Cationic Block Copolymer Micelle Size by pH and Ionic Strength," ACS Publications, American Chemical Society, Biomacromolecules, vol. 17, No. 9, https://doi.org/10.1021/acs.biomac.6b00654, Aug. 2016, pp. 2849-2859.

Cho et al., "Polycation gene delivery systems: escape from endosomes to cytosol," Journal of Pharmacy and Pharmacology, vol. 55, DOI 10.1211/0022357021206, Apr. 3, 2003, pp. 721-734.

Tockary et al., "Tethered PEG crowdedness determining shape and blood circulation profile of polyplex micelle gene carriers," American Chemical Society, ACS Publications, Macromolecules, vol. 46, Issue 16, https://doi.org/10.1021/ma401093z.s001, May 2013, 4 pp.

Li et al., "Toroidal Packaging of pDNA into Block Ionomer Micelles Exerting Promoted in Vivo Gene Expression," ACS Publications, American Chemical Society, BioMacromolecules, vol. 16, DOI: 10.1021/acs.biomac.5b00491, Jul. 30, 2015, pp. 2664-2671.

Wang et al., "Quantitation of Complexed versus Free Polymers in Interpolyelectrolyte Polyplex Formulations," American Chemical Society, ACS Macro Letters, vol. 2, Issue 11, https://doi.org/10.1021/mz400500q, Nov. 8, 2013, pp. 1038-1041.

Ramadurai et al., "Dynamic studies of the interaction of a pH responsive, amphiphilic polymer with a DOPC lipid membrane," Royal Society of Chemistry, Soft Matter, vol. 13, No. 20, DOI: 10.1039/c6sm02645a, May 28, 2017, pp. 3690-3700.

Wu et al., "Glucose-Containing Diblock Polycations Exhibit Molecular Weight, Charge, and Cell-Type Dependence for pDNA Delivery," ACS Publications, American Chemical Society, BioMacromolecules, vol. 15, No. 5, dx.doi.org/10.1021/bm5001229, Mar. 13, 2014, pp. 1716-1726.

Momot et al.," Pulsed Field Gradient Nuclear Magnetic Resonance as a Tool for Studying Drug Delivery Systems," Concepts in Magnetic Resonance Part A, 19A, vol. 2, (Applicant points out, in accordance with MPEP 609.04(a), that the year of publication, 2003, is sufficiently earlier than the effective U.S. filing date, so that the particular month of publication is not in issue.), 2003, pp. 51-64.

Zhang et al., "Quantifying Binding of Ethylene Oxide—Propylene Oxide Block Copolymers with Lipid Bilayers," HHS Public Access, Langmuir, vol. 33, No. 44, doi:10.1021/acs.langmuir.7b02279, Nov. 7, 2017, pp. 12624-12634.

So et al., "Rate of Molecular Exchange Through the Membranes of Ionic Liquid Filled Polymersomes Dispersed in Water,"American Chemical Society, ACS Publications, The Journal of Physical Chemistry C, vol. 118, No. 36, Aug. 28, 2014, pp. 21140-21147.

Zhang et al., "INfluence of Cholesterol and Bilayer Curvature on the Interaction of PPO-PEO Block Copolymers with Liposomes," HHS Public Acccess, Langmuir, vol. 35, No. 22, doi:10.1021/acs.langmuir.9b00572, Jun. 4, 2019, pp. 7231-7241.

Gary et al., "The Influence of Nano-Carrier Achitecture on In Vitro siRNA Delivery Performance and In Vivo Biodistribution: Polyplexes vs. Micelleplexes," NIH Public Access, ACS Nano, vol. 5, No. 5, doi:10.1021/nn102540y, May 24, 2011, pp. 3493-3505.

McLendon et al., "Poly(glycoamidoamine) Vehicles Promote pDNA Uptake through Multiple Routes and Efficient Gene Expression via Caveolae-Mediated Endocytosis," American Chemical Society, Molecular Pharmaceutics, vol. 7, No. 3, 10.1021/mp900282e, Mar. 29, 2010, pp. 738-750.

Doudna et al., "The new frontier of genome engineering with CRISPR-Cas9," Science, vol. 346, Issue 6213, DOI: 10.1126/science.1258096, Nov. 28, 2014, pp. 1258096-1-1258096-9.

Zetsche et al., "Cpf1 Is a Single RNA-Guided Endonuclease of a Class 2 CRISPR-Cas System," ELSEVIER Inc., Cell, No. 163, http://dx.doi.org/10.1016/j.cell.2015.09.038, Oct. 22, 2015, pp. 759-771.

Strecker et al., "Engineering of CRISPR-Cas 12b for human genome editing," Nature Communications, vol. 10, Article No. 212, https://doi.org/10.1038/s41467-018-08224-4, Jan. 22, 2019, 8 pp.

Kim et al., "Highly efficient RNA-guided genome editing in human cells via delivery of purified Cas9 ribonucleoproteins," Cold Spring

(56) References Cited

OTHER PUBLICATIONS

Harbor Laboratory Press, Genome Research, vol. 24, No. 6, https://doi.org/10.1101/gr.171322.113, Apr. 2, 2014, pp. 1012-1019.

Liu et al., "Delivery Strategies of the CRISPR-Cas9 Gene-Editing System for Therapeutic Applications," HHS Public Access, Journal of Controlled Release, vol. 266, doi:10.1016/j.jconrel.2017.09.012, Nov. 28, 2017, pp. 17-26.

Schumann et al., "Generation of knock-in primary human T cells using Cas9 ribonucleoproteins," Research Gate, PNAS, vol. 112, No. 33, DOI: 10.1073/pnas.1512503112, Aug. 18, 2015, pp. 10437-10442.

Niu et al., "Generation of Gene-Modified Cynomolgus Monkey via Cas9/RNA-Mediated Gene Targeting in One-Cell Embryos," ELSEVIER Inc., Cell, vol. 156, https://doi.org/10.1016/j.cell.2014.01.027, Feb. 13, 2014, pp. 836-843.

Chang et al., "Genome editing with RNA-guided Cas9 nuclease in Zebrafish embryos," NPG, Cell Research, vol. 23, No. 4, doi:10.1038/cr.2013.45, Mar. 26, 2013, pp. 465-472.

Lao et al., "HPV Oncogene Manipulation Using Nonvirally Delivered CRISPR/Cas9 or Natronobacterium gregoryi Argonaute," Advanced Science, vol. 5, Issue 7, DOI:10.1002/advs.201700540, May 18, 2018, 1700540, 12 pp.

Fu et al., "High frequency off-target mutagenesis induced by CRISPR-Cas nucleases in human cells," HHS Public Access, Nature Biotechnology, vol. 31, No. 9, doi:10.1038/nbt.2623, Sep. 2013, pp. 822-826.

Cradick et al., "CRISPR/Cas9 systems targeting B-globin and CCR5 genes have substantial off-target activity," Nucleic Acids Research, vol. 41, No. 20, doi: 10.1093/nar/gkt714, Aug. 11, 2013, pp. 9584-9592.

Xu et al., "Targeting of NLRP3 inflammasome with gene editing for the amelioration of inflammatory diseases," Nature Communications, vol. 9, Article No. 4092, DOI:10.1038/s41467-018-06522-5, Oct. 5, 2018, 14 pp.

Chen et al., "Targeted Delivery of CRISPR/Cas9-Mediated Cancer Gene Therapy via Liposome-Templated Hydrogel Nanoparticles," HHS Public Access, Advanced Functional Materials, vol. 27, No. 46, doi:10.1002/adfm.201703036, Dec. 8, 2017, 18 pp.

Zuris et al., "Cationic lipid-mediated delivery of proteins enables efficient protein-based genome editing in vitro and in vivo," Nature Biotechnology, vol. 33, No. 1, https://doi.org/10.1038/nbt.3081, Oct. 30, 2014, pp. 73-80.

Wang et al., "Efficient delivery of genome-editing proteins using bioreducible lipid nanoparticles," Proceedings of the National Academy of Sciences of the United States of America, PNAS, vol. 113, No. 11, https://doi.org/10.1073/pnas.1520244113, Mar. 15, 2016, pp. 2868-2873.

Mout et al., "Efficient Gene Editing through Direct Cytosolic Delivery of CRISPR/Cas0-Ribonucleoprotein," HHS Public Access, ACS Nano, vol. 11, No. 3, https://doi.org/10.1021/acsnano.6b07600, Jan. 27, 2017, pp. 2452-2458.

Wang et al., "Genome Editing for Cancer Therapy: Delivery of Cas9 Protein/sgRNA Plasmid via a Gold Nanocluster/Lipid Core-Shell Nanocarrier," Advanced Science, vol. 4, No. 11, DOI:10.1002/advs.201700175, Sep. 7, 2017, 10 pp.

Hansen-Bruhn et al., "Active Intracellular Delivery of a Cas9/sgRNA Complex Using Ultrasound-Propelled Nanomotors," Research Gate, Angewandte Chemie, vol. 57, Issue 10, Mar. 1, 2018, pp. 2657-2661.

Ramakrishna et al., "Gene distruption by cell-penetrating peptide-mediated delivery of Cas9 protein and guide RNA," Cold Spring Harbor Laboratory Press, Genome Research, vol. 24, No. 6, https://doi.org/10.1101/gr.171264.113, Apr. 2, 2014, pp. 1020-1027.

Wang et al., "Nonviral gene editing via CRISPR/Cas9 delivery by membrane-disruptive and endosomolytic helical polypeptide," Proceedings of the National Academy of Sciences of the United States of America, PNAS, vol. 115, No. 19, https://doi.org/10.1073/pnas.1712963115, May 8, 2018, pp. 4903-4908.

Lostale-Seijo et al., "Peptide/Cas9 nanostructures for ribonucleoprotein cell membrane transport and gene edition," Royal Society of Chemistry, Chemical Science, vol. 8, Issue 12, DOI: 10.1039/c7sc03918b, Oct. 18, 2017, pp. 7923-7931.

Yue et al., "Graphene oxide-mediated Cas9/sgRNA delivery for efficient genome editing," Royal Society of Chemistry, Nanoscale, vol. 10, Issue 3, DOI: 10.1039/c7nr07999k, Dec. 17, 2017, pp. 1063-1071.

Zhou et al., "Enhanced Cytosolic Delivery and Releases of CRISPR/Cas9 by Black Phosphorus Nanosheets for Genome Editing," Angewandte Chemie, vol. 57, No. 32, https://doi.org/10.1002/anie.201806941, Jun. 25, 2018, pp. 10268-10272.

Chen et al., "A Universal GSH-Responsive Nanoplatform for the Delivery of DNA, mRNA, and Cas9/sgRNA Ribonucleoportein," HHS Public Access, ACS Applied Materials & Interfaces, vol. 10, No. 22, https://doi.org/10.1021/acsami.8b03496, Jun. 6, 2018, pp. 18515-18523.

Wang et al., "Versatile Redox-Reponsive Polyplexes for the Delivery of Plasmid DNA, Messenger RNA, and CRISPR-Cas9 Genome-Editing Machinery," HHS Public Access, ACS Applied Materials & Interfaces, vol. 10, No. 38, doi:10.1021/acsami.8b09642, Sep. 26, 2018, pp. 31915-31927.

Osborn et al., "Fanconi Anemia Gene Editing by the CRISPR/Cas9 System," Human Gene Therapy, vol. 26, No. 2, DOI: 10.1089/hum.2014.111, Feb. 2015, pp. 114-126.

Carlson-Stevermer et al., "Assembly of CRISPR ribonucleoproteins with biotinylated oligonucleotides via an RNA aptamer for precise gene editing," Nature Communications, vol. 8, Issue 1, Article 1711, DOI:10.1038/s41467-017-01875-9, Nov. 23, 2017, 13 pp.

Brinkman et al., "Easy quantitative assessment of genome editing by sequence trace decomposition," Nucleic Acids Research, vol. 42, No. 22, doi: 10.1093/nar/gku936, Sep. 24, 2014, pp. e168-e168.

Ogris et al., "The size of DNA/transferrin-PEI complexes is an important factor for gene expression in cultured cells," Gene Therapy, vol. 5, No. 10, https://doi.org/10.1038/sj.gt.3300745, Oct. 14, 1998, pp. 1425-1433.

Luo et al., "Enhancement of transfection by phyiscal concentration of DNA at the cell surface," Research Gate, Nature America, Nature Biotechnology, vol. 18, No. 8, https://doi.org/10.1038/78523, Sep. 2000, pp. 893-895.

Carpenter et al., "CellProfiler: image analysis software for identifying and quantifying cell phenotypes," BMC, Genome Biology, vol. 7, No. 10, Article R100, doi:10.1186/gb-2006-7-10-r100, Oct. 31, 2006, 11 pp.

Kamentsky et al., "Improved structure, function and compatibility for CellProfiler: modular high-throughput image analysis software," Oxford Academic, ISCB, International Society for Computational Biology, Bioinformatics, vol. 27, Issue 8, https://doi.org/10.1093/bioinformatics/btr095, Apr. 15, 2011, pp. 1179-1180.

Boutros et al., "Microscopy-Based High-Content Screening," ELSEVIER Inc., CrossMark, Cell Press, vol. 163, Issue 6, https://doi.org/10.1016/j.cell.2015.11.007, Dec. 3, 2015, pp. 1314-1325.

Simm et al., "Repurposing High-Throughput Image Assays Enables Bioogical Activity Prediction for Drug Discovery," ELSEVIER Ltd., CellPress, Cell Chemical Biology, vol. 25, No. 6, https://doi.org/10.1016/j.chembiol.2018.01.015, May 17, 2018, pp. 611-618.

Kang et al., "Improving drug discovery with high-content phenotypic screens by systematic selection of report cell lines," HHS Public Access, Nature Biotechnology, vol. 34, No. 1, doi:10.1038/nbt.3419, Jan. 2016, pp. 70-77.

Steyer et al., "High content analysis platform for optimization of lipid mediated CRISPR-Cas9 delivery strategies in human cells," ScienceDirect, ELSEVIER, Acta Biomaterialia, vol. 34, https://doi.org/10.1016/j.actbio.2015.12.036, Apr. 1, 2016, pp. 143-158.

"CellProfiler | Free open-source software for measuring and analyzing cell images," accessed from https://cellprofiler.org/examples#cellparticle-counting-and-scoring-the-percentage-of-stained-objects, accessed on Jun. 20, 2019, 25 pp.

Tan et al., "Block Polymer Micelles Enable CRISPR/Cas9 Ribonucleoprotein Delivery Physiochemical Properties Affect Packaging Mechanisms and Gene Editing Efficiency," American Chemical Society, Macromolecules, vol. 52, DOI: 10.1021/acs.macromol.9b01645, Oct. 21, 2019, pp. 8197-8206.

Tan et al., "Polycation Architecture and Assembly Direct Successful Gene Delivery: Micelleplexes Outperform Polyplexes via Optimal

(56) References Cited

OTHER PUBLICATIONS

DNA Packaging," American Chemical Society, Journal of the American Chemical Society, vol. 141, DOI: 10.1021/jacs.9b06218, Sep. 25, 2019, pp. 15804-15817.
Reineke, "Self Assembly of Amphiphilic Block Polymers Promote Encapsulation of DNA and Cas9 Payloads and Intracellular Delivery," Powerpoint Presentation at the Polymers in Medicine and Biology ACS POLY Workshop, University of Minnesota, Department of Chemistry, Sep. 18, 2018, 40 pp.

* cited by examiner

CATIONIC BLOCK POLYMER MICELLES FOR DELIVERY OF BIOLOGICAL AGENTS

This application claims the benefit of U.S. Provisional Patent Application No. 62/897,660, filed on Sep. 9, 2019, the entire content of which is incorporated herein by reference.

GOVERNMENT INTEREST

This invention was made with government support under DMR-1420013 awarded by National Science Foundation (NSF) and Grant No. N660011824041 awarded the Department of Defense/Defense Advanced Research Projects Agency (DARPA). The government has certain rights in the invention.

BACKGROUND

Polymeric gene delivery vehicles are an essential tool in life science research and have the potential to be used in clinical gene therapy due to their versatility, relative low production cost, and low immunogenicity. Synthetic polymers have been used to deliver biomacromolecule payloads such as, for example, plasmid DNA (pDNA), ribonucleoprotein (RNP), and the like, due to their versatility, low toxicity, and the ability to encapsulate large payloads. Some recent examples indicate that synthetic polymer-based systems achieved biomacromolecule based gene delivery and gene editing both in vitro and in vivo.

For example, in aqueous physiological solutions, cationic polymers can spontaneously bind with negatively charged pDNA and form interpolyelectrolyte complexes. These complexes are predominately internalized by various endocytic routes, followed by cargo release from these vesicles inside the cells via different proposed mechanisms, and subsequent entry into the cell nucleus to promote gene expression. Compared to viral vehicles, polymeric delivery systems typically have lower delivery efficiency, and various optimization strategies have been applied to improve this parameter such as, for example, changing the cationic moieties on polymers, adding targeting ligands, and installing responsive monomers, which can improve uptake efficiency and help to balance transfection efficiency and cytotoxicity.

In one example, polyplexes formed with block copolymers consisting of distinct hydrophilic and cationic blocks exhibit significant compaction of pDNA, and have been shown to promote colloidal stability in biological media in addition to high transfection efficiency. In comparison, amphiphilic block copolymers self-assemble into micelles in solution, where cationic micelles complex with pDNA to form micelleplexes. Polymeric micelles are well established delivery vehicles for small molecule drugs and have demonstrated efficient delivery of siRNA, but are relatively underexplored for pDNA delivery.

In another example, CRISPR (clustered, regularly interspaced, short palindromic repeats)/Cas9 (CRISPR-associated protein 9)-based genome editing has rapidly emerged as a multi-faceted technology to enable gene insertion, deletion, activation, suppression, and even single base editing of target genes within the nucleus of any cell. This highly efficient and facile technique has broad utility from white biotechnology and agriculture to biomedical research, pharmaceutics, and regenerative medicine.

Currently, the CRISPR/Cas9 system can be delivered in vitro, ex vivo, and in vivo in three different payload forms: i) pDNA that encodes Cas9 protein and/or sgRNA ii) mRNA that encodes for Cas9 nuclease and a separate sgRNA, or iii) a ribonucleoprotein (RNP) that consists of recombinant Cas9 protein precomplexed directly with a sgRNA. While engineered viruses have shown exceptional delivery efficiency and expression of Cas9 protein in cells, limitations such as immunogenicity and size restrictions in packaging exist. Physical delivery methods such as electroporation and microinjection are known to cause cell damage or death and are challenging to apply to a large population of cells/tissues.

CRISPR-Cas9 pDNA needs to enter the cellular nucleus to express, and consistent expression produces an overabundance of Cas9 protein, which can lead to increased off-target editing and mutagenesis. Researchers have utilized the CRISPR/Cas9 system in mRNA form to circumvent the barrier of nuclear entry, which has been reported with polymer-based nanoparticles. However, sgRNA often needs to be delivered separately, presenting challenges in trafficking kinetics of different payloads.

Direct delivery of CRISPR/Cas9 ribonucleoprotein (RNP), on the other hand, has several benefits, including precision in endonuclease dosing and potential to avoid uncontrolled integration of the transgene into the cellular genome. While different CRISPR/Cas9 RNP delivery systems have been recently explored, such as lipid-based nanoparticles, gold nanoparticles, cell penetrating peptides, and other hybrid nanostructures, the mechanisms of payload encapsulation and the resultant complexes are generally not quantitatively understood/characterized. Polymers offer a well-documented pharmaceutically-relevant platform that have been underexplored for RNP encapsulation and delivery, and only limited number of reports have been presented, likely due to the inherent structural, charge, and binding differences of plasmid and protein-based payloads.

To this end, designing novel and efficient polymer micelle-based pDNA and RNP delivery vehicles, as well as improving the fundamental understanding of polymer-cargo complex composition and architecture on pDNA and protein loading and delivery efficiency, are necessary for advanced applications.

SUMMARY

In general, the present disclosure is directed to polymer micelles that provide a well-defined host to bind with biological agents and facilitate intracellular delivery thereof. In one embodiment, the polymer micelles include a diblock copolymer with a hydrophobic block with monomeric units chosen from alkyl (meth)acrylates, alkyl (meth)acrylamides, and combinations thereof; and a hydrophilic cationic block including monomeric units chosen from alkylamino (meth) acrylates, alkylamino (meth)acrylamides, and combinations thereof.

In the present application, (meth)acrylates include acrylates and methacrylates, (meth)acrylamides include acrylamides and methacrylamides, alkylamino (meth)acrylates include alkylaminoacrylates and alkylamino methacrylates, and alkylamino(meth)acrylamides include alkylamino acrylamides and alkylamino methacrylamides.

The copolymer is in the form of a micelle including a central core derived from the hydrophobic block and shell at least partially surrounding the core, wherein the shell includes a plurality of filamentous arms derived from the hydrophilic block and emanating outward from the core. The arms form a cationic brush-like corona on the micelle surface that facilitates binding and encapsulation of a biological agent.

In another embodiment, the polymer micelles include a tri-block polymer with a hydrophobic block having monomeric units chosen from alkyl (meth)acrylates, alkyl (meth)acrylamides, and combinations thereof; a hydrophilic cationic block including monomeric units chosen from alkylamino (meth)acrylates, alkylamino (meth)acrylamides, and combinations thereof, and a hydrophilic nonionic block including ethylene glycol (PEG) monomeric units. The terpolymer is in the form of a micelle including a central core derived from the hydrophobic block and shell at least partially surrounding the core. The shell includes a plurality of filamentous arms in which the hydrophilic cationic block forms a first portion of the arms proximal the core, and the hydrophilic nonionic block forms a second portion of the arms connected to the first portion of the arms and distal the core.

In some embodiments, the micelles can complex with anionic biomacromolecular cargos to form micelleplexes, which in some cases can achieve excellent pDNA delivery and protein expression in multiple cell lines. In another embodiment, the micelles can achieve excellent CRISPR-Cas9 RNP delivery and gene editing efficiency with engineered HEK 293T (human embryonic kidney) cells. The delivery system of the present disclosure provides a well-defined nonviral delivery vehicle for both nucleic acids and protein-based gene editing tools.

In one aspect, the present disclosure is directed to a compound including an amphiphilic polymer with a hydrophobic block including monomeric units chosen from alkyl (meth)acrylates, alkyl (meth)acrylamides, and combinations thereof; and a hydrophilic cationic block including monomeric units chosen from alkylamino (meth)acrylates, alkylamino (meth)acrylamides, and combinations thereof. The polymer is in the form of a micelle with a central core derived from the hydrophobic block and shell at least partially surrounding the core. The shell includes a plurality of filamentous arms derived from the hydrophilic block and emanating outward from the core. A biological agent is associated with the arms of the micelle.

In another aspect, the present disclosure is directed to a compound including an amphiphilic polymer, which includes
a hydrophobic block with monomeric units chosen from alkyl (meth)acrylates, alkyl (meth)acrylamides, and combinations thereof;
a hydrophilic cationic block with monomeric units chosen from alkylamino (meth)acrylates, alkylamino (meth)acrylamides, and combinations thereof; and
a hydrophilic nonionic block including ethylene glycol (PEG) monomeric units.
The polymer is in the form of a micelle with a central core derived from the hydrophobic block and shell at least partially surrounding the core, wherein the shell includes a plurality of filamentous arms derived from the hydrophilic block and emanating outward from the core. The hydrophilic cationic block forms a first portion of the arms proximal the core and the hydrophilic nonionic block forms a second portion of the arms connected to the first portion of the arms and distal the core. A biological agent is associated with the arms of the micelle.

In another aspect, the present disclosure is directed to a method, including:
applying to a cell a composition, the composition including:
(a) an aqueous pharmaceutically acceptable liquid carrier; and
(b) an amphiphilic polymer, including:
a hydrophobic block with monomeric units chosen from alkyl (meth)acrylates, alkyl (meth)acrylamides, and combinations thereof, and
a hydrophilic cationic block including monomeric units chosen from alkylamino (meth)acrylates, alkylamino (meth)acrylamides, and combinations thereof; and
wherein the amphiphilic polymer is in the form of a micelle with a central core derived from the hydrophobic block and shell at least partially surrounding the core, wherein the shell includes a plurality of filamentous arms derived from the hydrophilic block and emanating outward from the core; and
(c) a biological payload associated with the arms of the micelle, wherein the biological payload is delivered into the cell.

In another aspect, the present disclosure is directed to a method for delivering a biological agent into a cell, the method including:
in a composition including a pharmaceutically acceptable liquid carrier and an amphiphilic terpolymer, the amphiphilic terpolymer including:
a hydrophobic block with linear alkyl (meth)acrylate monomeric units;
a hydrophilic cationic block with alkyl amino (meth) acrylate monomeric units; and
a hydrophilic nonionic block including ethylene glycol (PEG) monomeric units;
wherein the terpolymer is in the form of a micelle in the liquid carrier. The micelle includes comprising a central core derived from the hydrophobic block and shell at least partially surrounding the core. The shell includes a plurality of brush-like arms derived from the hydrophilic blocks and emanating radially from the core, and wherein the hydrophilic cationic block forms a first portion of the arms proximal the core and the hydrophilic nonionic block forms a second portion of the arms connected to the first portion of the arms and distal the core;
electrostatically bonding a biological agent with the spherical micelle; and
applying the composition to a cell such that the biological agent is delivered into the cell.

In another aspect, the present disclosure is directed to a micelleplex including a plurality of amphiphilic micelles, wherein at least a portion of the amphiphilic micelles are bonded to a biological agent. The amphiphilic micelles each include:
a hydrophobic block with monomeric units chosen from alkyl (meth)acrylates, alkyl (meth)acrylamides, and combinations thereof; and
a hydrophilic cationic block with monomeric units chosen from alkylamino (meth)acrylates, alkylamino (meth)acrylamides, and combinations thereof. Each amphiphilic micelle includes a central core derived from the hydrophobic block, and shell at least partially surrounding the core. The shell includes a plurality of filamentous arms derived from the hydrophilic block and emanating outward from the core.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 1(b) is schematic representation of substantially spherical micelles formed from the amphiphilic polymers DB and ODB. ODB(2), ODB(5), and ODB(10) represent for ODB micelles with 2 kDa, 5 kDa, and 10 kDa PEG block length, respectively.

FIG. 1(c) is a schematic representation of a process in which a biological agent payload (CRISPR-Cas9 ribonucleoprotein (RNP)) is bound to a micelle of FIG. 1(b) to form a micelleplex.

FIG. 3(a) shows micelles only, and FIG. 3(b) shows micelleplexes at polymer:RNP molar ratio of 2.5:1 (denoted as 2.5) or 5:1 (denoted as 5). The asterisks "*" indicate statistically different ($p<0.05$) analyzed by one-way ANOVA followed by a post hoc Tukey test.

FIG. 10(a) plots percent mCherry+ cells measured 48 h post-transfection by flow cytometry. Data presented as mean standard deviation (n=3). The asterisks indicate statistically different ($p<0.05$) analyzed by one-way ANOVA followed by a post hoc Tukey test. FIG. 10(b) plots the percent total NHEJ editing measured by capillary Sanger sequencing and TIDE assay. Data were acquired from the same batch of samples for flow cytometry analysis. Cells from all three wells of the triplicated transfection were combined, and DNA was extracted for sequencing analysis. FIG. 10(c) illustrates representative chromatograms of the sequencing data acquired by transfection with micelleplexes formed in water: 20 bp sgRNA binding region of untreated cells (top) and the cells treated with ODB(10) micelleplexes at polymer:RNP=2.5:1 (bottom).

FIGS. 14(a)-(e) are plots of size distributions of a) D polymer, b) OD polymer, c) DB micelle, d) ODB micelle, (e) jetPEI (a commercial positive control) and their complexes with pDNA in PBS at N/P=5, while FIG. 14(f) is a plot of the ζ potential of the polymers (a)-(d) in PBS at N/P=5.

FIGS. 15(a)-(b) are plots of GFP expression in HeLa cells (top) and cell viability (%) as measured by a CCK-8 cytotoxicity assay (bottom) 48 h after transfection (n=3). FIG. 15(b) is a plot of GFP expression in HEK 293T cells (top) and cell viability (%) as measured by a CCK-8 cytotoxicity assay (bottom) 48 h after transfection (n=3). Data are presented as mean±standard deviation. The "+" symbols indicate statistically higher compared to jetPEI control ($p<0.05$). The "=" symbols indicate statistical equivalence between the means of the samples ($p>0.5$). Data were analyzed by one-way ANOVA followed by a post hoc Tukey test.

FIG. 16(a) shows percent $Cy5_+$ cells and percent $GFP_+$ cells. FIG. 16(b) shows percent $GFP_+$ cells out of $Cy5_+$ cells [(# of $GFP_+$ cells)/(# of $Cy5_+$ cells)*100%]. The "*" symbols indicate statistically difference ($p<0.05$). Data analyzed by unpaired t test. FIG. 16(c) shows flow cytometry scattered plot of cells that undergo internalization and GFP expression. Q1 denotes $Cy5_+$ $GFP_-$ cells, Q2 denotes $Cy5_+$ $GFP_+$ cells, Q3 denotes $Cy5_-$ $GFP_+$ cells, Q4 denotes $Cy5_-$ $GFP_-$ cells.

FIG. 18(a) is a plot of the experimental and fitted echo decay curves of the protons from the O block in OD polymer and OD polyplexes at N/P=5 in PBS buffer in $D_2O$ at 23° C. The $\Delta$=500 ms and $\delta$=5 ms. FIG. 18(b) is a Berry plot of ODB micelleplexes in PBS buffers at N/P=5.

FIG. 21(a) shows a plot of the size distributions from dynamic light scattering analysis of ODB micelles, 2-oleoyl-1-palmitoyl-sn-glycero-3-phosphocholine (POPC) liposomes, and the mixture of ODB micelles with POPC liposomes. FIG. 21(b) shows echo decay curves from pulse field gradient NMR of the protons from O block in ODB micelle only and ODB micelle in presence of POPC liposome in deuterated PBS buffer at 23° C. The $\Delta$=600 ms and $\delta$=5 ms.

Like symbols in the drawings indicate like elements.

DETAILED DESCRIPTION

Figure 1:
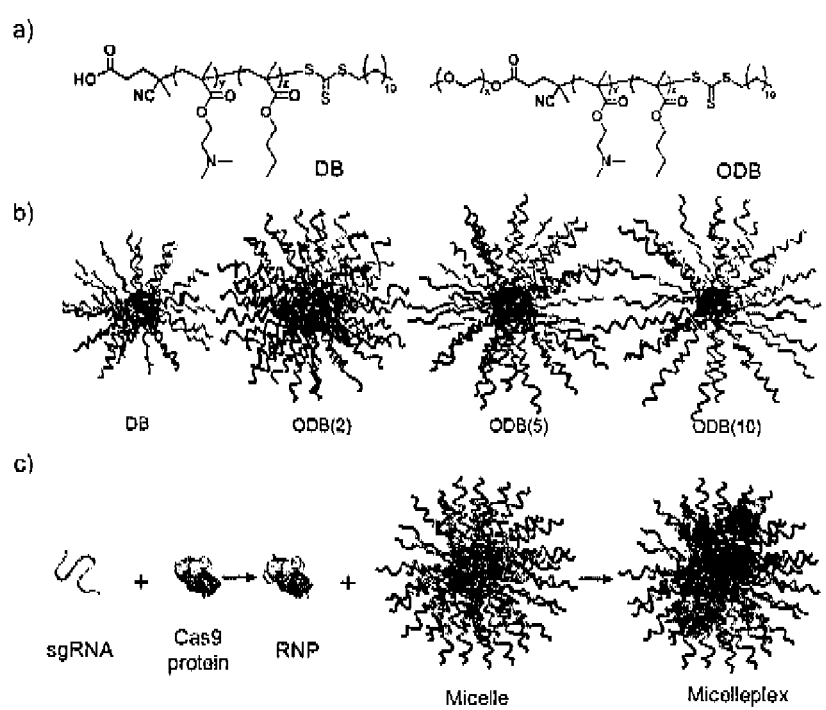
FIG. 1(*a*) is a schematic representation of an amphiphilic diblock copolymer poly(2-(dimethylamino)ethyl methacrylate)-block-poly(n-butyl methacrylate) (DB) and an amphiphilic triblock polymer poly(ethylene glycol)-block-poly(2-(dimethylamino)ethyl methacrylate)-block-poly(n-butyl methacrylate) (ODB).

In one embodiment, the polymeric micelles of the present disclosure include an amphiphilic diblock copolymer with a hydrophobic block and a hydrophilic cationic block. The hydrophobic block includes monomeric units chosen from alkyl (meth)acrylates, alkyl (meth)acrylamides, and combinations thereof, wherein (meth)acrylates include acrylates and methacrylates, and (meth)acrylamides include acrylamides and methacrylamides. The micelles bind with biological agents through electrostatic interactions, enable quantitative characterization of biological agent packaging, and facilitate intracellular delivery of the biological agent, effective protein expression and genome editing.

As used herein, the term monomer, unless otherwise indicated, includes both isolated monomers and residues of monomers in an oligomer or a polymer (i.e. repeat units or residues).

The alkyl (meth)acrylate and alkyl (meth) acrylamide monomeric units in the hydrophobic block can include a wide variety of alkyl groups, which may be linear or branched, substituted or unsubstituted, and includes cycloalkyls. In various embodiments, the linear or branched alkyl groups in each monomeric unit can include 2 to 10 carbon atoms, or 3 to 7 carbon atoms, or 3 to 5 carbon atoms. The chain length of the hydrophobic block can vary widely depending on the intended application, and in some embodiments is about 1 kDa to about 40 kDa, or about 10 kDa to about 25 kDa. In some embodiments, which are not intended to be limiting, the hydrophobic block includes poly(n-butyl methacrylate) (PnBMA).

The hydrophilic cationic block of the amphiphilic diblock copolymer includes monomeric units chosen from alkylamino (meth)acrylates, alkylamino (meth)acrylamides, and combinations thereof, wherein (meth)acrylates include acrylates and methacrylates, and (meth)acrylamides include acrylamides and methacrylamides. The alkylamino (meth) acrylate and alkylamino (meth) acrylamide monomeric units in the hydrophilic block can include a wide variety of alkyl groups, which may be linear or branched. In various embodiments, the linear or branched alkyl groups in each monomeric unit can include 2 to 5 carbon atoms. The term alkylamino, which includes cycloalkylamino, as used herein, refers to an NHRp, or an NRpRq group, wherein Rp and Rq can be alkyl, or cycloalkyl. The term dialkylamino, as used herein, refers to an NRpRq group, wherein Rp and Rq can be alkyl or cycloalkyl.

The chain length between the polymer backbone and the tertiary amine can also be varied and may include 2-5 methylenes, for example, methyl, ethyl propyl, and butyl groups.

The chain length of the hydrophilic block can vary widely depending on the intended application, and in some embodiments is about 1 kDa to about 40 kDa, or about 15 kDa to about 25 kDa. In some embodiments, which are not intended to be limiting, the hydrophilic block includes poly(2-(dimethylamino)ethyl methacrylate) (PDMAEMA).

When placed in an appropriate aqueous liquid carrier, the amphiphilic diblock copolymer forms a micellar structure including a central core derived from the hydrophobic block. In various embodiments, the radius of the core is about 5 to about 20 nm, or about 8 to about 11 nm.

A shell, which at least partially surrounds the core, includes a plurality of filamentous arms derived from the hydrophilic block. The arms emanate outward from the core and form a cationic brush corona on the micelle surface that facilitates binding and encapsulation of biological agents. In various embodiments, which are not intended to be limiting, the length of the arms is about 10 nm to about 50 nm, or about 15 nm to about 25 nm. In various embodiments, the shell includes about 10 to about 5000 arms, or about 50 to about 250 arms. The length and geometry of the arms can be selected to provide molecular flexibility during the binding step with a particular biological agent, or to ensure the availability of the bound biological agent for its target. The length and composition of the arms may thus improve the biological activity of the delivery vehicles of the present disclosure, and make the delivery vehicles easier to prepare. In some embodiments, the flexibility of the arms may be also be configured to conformationally adapt for binding to a target biological agent or sequence. In addition, the morphology of the micelle may be configured to orient a biological agent or molecule for optimal reaction with a target or entry into a cellular structure.

In another embodiment, the polymeric micelles of the present disclosure include an amphiphilic tri-block polymer (also referred to herein as a terpolymer) with a hydrophobic block, a hydrophilic cationic block, and a hydrophilic nonionic block.

The hydrophobic block includes monomeric units chosen from alkyl (meth)acrylates, alkyl (meth)acrylamides, and combinations thereof, wherein (meth)acrylates include acrylates and methacrylates, and (meth)acrylamides include acrylamides and methacrylamides. The alkyl (meth)acrylate and alkyl (meth) acrylamide monomeric units in the hydrophobic block can include a wide variety of alkyl groups, which may be linear or branched. In various embodiments, the linear or branched alkyl groups in each monomeric unit can include 2 to 10 carbon atoms, or 3 to 7 carbon atoms, or 3 to 5 carbon atoms. The alkyl groups may be substituted or unsubstituted, and may include cycloalkyls.

The chain length of the hydrophobic block can vary widely depending on the intended application, and in some embodiments is about 1 kDa to about 40 kDa, or about 10 kDa to about 25 kDa. In some embodiments, which are not intended to be limiting, the hydrophobic block includes poly(n-butyl methacrylate) (PnBMA).

The hydrophilic cationic block of the amphiphilic terpolymer includes monomeric units chosen from alkylamino (meth)acrylates, alkylamino (meth)acrylamides, and combinations thereof, wherein (meth)acrylates include acrylates and methacrylates, and (meth)acrylamides include acrylamides and methacrylamides. The alkylamino (meth)acrylate and alkylamino (meth) acrylamide monomeric units in the hydrophilic cationic block can include a wide variety of alkyl groups, which may be linear or branched. In various embodiments, the linear or branched alkyl groups in each monomeric unit can include 2 to 5 carbon atoms. As with the diblock copolymer above, the term alkylamino, which includes cycloalkylamino, as used herein, refers to an NHRp, or an NRpRq group, wherein Rp and Rq can be alkyl, or cycloalkyl. The term dialkylamino, as used herein, refers to an NRpRq group, wherein Rp and Rq can be alkyl or cycloalkyl.

The chain length between the polymer backbone and the tertiary amine can also be varied and may include 2-5 methylenes, for example, methyl, ethyl propyl, butyl, groups, and the like.

The chain length of the hydrophilic cationic block can vary widely depending on the intended application, and in some embodiments is about 1 kDa to about 40 kDa, or about 15 kDa to about 25 kDa. In some embodiments, which are not intended to be limiting, the hydrophilic cationic block includes poly(2-(dimethylamino)ethyl methacrylate) (PDMAEMA).

The amphiphilic terpolymer further includes a hydrophilic nonionic block formed from ethylene glycol (PEG) monomeric units. The chain length of the hydrophilic nonionic block can vary widely depending on the intended application, and in some embodiments is about 1 kDa to about 40 kDa, or about 2 kDa to about 10 kDa.

When placed in an appropriate aqueous liquid carrier, the amphiphilic terpolymer forms a micellar structure including a central core derived from the hydrophobic block. In various embodiments, the radius of the core is about 5 to about 20 nm, or about 8 to about 11 nm.

A shell, which at least partially surrounds the core, includes a plurality of filamentous arms derived from the hydrophilic cationic block. The arms emanate outward from the core and form a cationic brush-like configuration on the micelle surface that facilitates binding and encapsulation of biological agents. In various embodiments, which are not intended to be limiting, the hydrodynamic length of the arms is about 10 nm to about 50 nm, or about 15 nm to about 25 nm. In various embodiments, the shell includes about 10 to about 5000 arms, or about 50 to about 250 arms.

Each of the arms in the shell further include a tip at an end distal the core, which is derived from the hydrophilic nonionic block. In other words, each arm includes a first portion, which is derived from the hydrophilic cationic block, connected to the core, and a second portion, derived from the hydrophilic nonionic block, connected to the first portion and distal the core. The arms form a corona-like shape, which in some embodiments can facilitate bonding with a selected biological agent.

The micellar structures formed by the hydrophobic blocks and the hydrophilic blocks of the amphiphilic di- and tri-block polymers and can have a wide variety of shapes, depending on, for example, the liquid carrier in which the diblock copolymer and terpolymer reside, the composition of the monomeric units making up the core portion and the arm portion, the overall length of the polymeric blocks, and number of polymer chains in the structure. For example, the micellar structure may be formulated to include about 30 to about 5000 polymer chains (also referred to herein as the micelle aggregation number), which can greatly impact the overall morphology of the structure. In various embodiments, which are not intended to be limiting, the micellar structures formed by the amphiphilic di- and tri-block polymers can include shapes such as spheroidal, including oblate spheroids and prolate spheroids, rod-like, worm-like, ring-like, vesicular, and combinations thereof.

In some embodiments, when placed in an appropriate liquid carrier, the hydrophobic blocks and the hydrophilic blocks of the amphiphilic di- and tri-block polymers self-assemble to form a micellar structure. In this application the term self-assemble means that the polymeric blocks align with one another in an organized structure or pattern of building blocks. The interactions between the hydrophobic blocks and the hydrophilic cationic blocks can arise from any of van der Waals attraction, electrostatic charge interaction or electronic (e.g., charge transfer) interaction, hydrogen bonding or metal-ligand interaction, the combination of which cause the hydrophobic and hydrophilic blocks to align with one another to form a desired micellar structure for delivery of a selected biological agent. In some embodiments, the hydrophobic and cationic hydrophilic blocks align with each other without any type of external direction to form a micellar structure of a desired shape or size.

In some embodiments, the amphiphilic polymers can be forced to assume a particular micellar morphology by modifying the composition, adding buffering agents, adjusting the solvent type, pH, the temperature, or other properties of the liquid carrier.

In one non-limiting example, FIG. 1(*a*) schematically illustrates an amphiphilic diblock copolymer DB that includes a hydrophobic block of poly(n-butyl methacrylate) (PnBMA), and a hydrophilic cationic block of poly(2-(dimethylamino)ethyl methacrylate) (PDMAEMA). In addition, FIG. 1(*a*) further illustrates an amphiphilic triblock polymer ODB including a hydrophobic block of poly(n-butyl methacrylate) (PnBMA), a hydrophilic cationic block of poly(2-(dimethylamino)ethyl methacrylate) (PDMAEMA), and a nonionic hydrophilic block of poly(ethylene glycol)(PEG).

FIG. 1(*b*) schematically illustrates substantially spherical micelles formed from the amphiphilic polymers DB and ODB. The micelle formed from the amphiphilic polymer DB includes a core and a plurality of brush-like filamentous arms extending outward from the core and forming a shell-like configuration about the core. The core is formed from the hydrophobic block and the arms are formed from the hydrophilic block. The micelle formed from the amphiphilic terpolymer ODB includes also includes a core and a plurality of brush-like filamentous arms extending outward from the core and forming a shell-like configuration about the core. The core is formed from the hydrophobic block and the arms are formed from the hydrophilic cationic block. In the ODB micelle, the arms further include a corona portion on the end of each arm derived from the hydrophobic nonionic block. The substantially spherical micelles ODB(2), ODB (5) and ODB (10) in FIG. 1(b) show that the micelles may be configured with from arms having increasing length (molecular weight).

The amphiphilic diblock copolymers and terpolymers described above are configured to bind with a biological agent. In various embodiments, which are not intended to be limiting, the biological agent is chosen from a peptide fragment, nuclease, a nucleic acid encoding a nuclease, oligo nucleotide, a protein, peptide a DNA editing template, guide RNA, a therapeutic agent (such as, for example, a drug), a plasmid DNA encoding protein, siRNA, monoclonal antibodies, Cas9 mRNA, and mixtures and combinations thereof. In various embodiments, the micellar polymers are configured to bind with plasmid DNA (pDNA), which encode protein (fluorescence or therapeutic); pDNA encode Cas9 nuclease and/or sgRNA; mRNA that encodes for proteins (fluorescence or therapeutic), Cas9 nuclease and a separate sgRNA; or a ribonucleoprotein (RNP) that consists of recombinant Cas9 protein precomplexed directly with a sgRNA.

In various embodiments, peptide fragments include two or more amino acids covalently linked by at least one amide bond (i.e. a bond between an amino group of one amino acid and a carboxyl group of another amino acid selected from the amino acids of the peptide fragment). The terms polypeptide and peptide fragments are used interchangeably. The term peptide fragment includes salts thereof, including pharmaceutically acceptable salts. For example, in some embodiments the peptide fragments may include pDNA encoded fluorescence or therapeutic proteins.

In various embodiments, DNA editing templates include an exogenous strand of DNA that bears homology arms to a section of genomic DNA that has been cut by a nuclease (for example, CAS9, TALEN or zinc finger) along with an intervening sequence between these homology arms that differs with the natural segment of genomic DNA that has been cut. This intervening segment selves as the template for repair of the cut genomic DNA and, in so doing, the cell corrects its own DNA to match that of the DNA template. The DNA template may be included in a single DNA expression vector that also encodes the nuclease.

The term guide RNA includes an engineered, non-naturally occurring Clustered Regularly Interspaced Short Palindromic Repeats (CRISPR) guide RNA that hybridizes with a target nucleic acid sequence of interest.

The term Cas9 mRNA includes a nucleotide sequence encoding a Type-II Cas9 protein, pDNA that encodes Cas9 protein, and pDNA that encode sgRNA. The CRISPR-Cas system is useful for precise editing of genomic nucleic acids (e.g., for creating null mutations). In such embodiments, the CRISPR guide RNA and/or the Cas enzyme may be expressed. For example, a composition containing only the guide RNA can be administered to an animal or cells transgenic for the Cas9 enzyme. Similar strategies may be used (e.g., designer zinc finger, transcription activator-like effectors (TALEs) or homing meganucleases).

The CRISPR-Cas system is known in the art for deleting, modifying genome sequences or incorporating transgenes. Transgene refers to any nucleotide sequence, particularly a DNA sequence, that is integrated into one or more chromosomes of a host cell by human intervention, such as by the methods of the present invention. For example, a transgene can be an RNA coding region or a gene of interest, or a nucleotide sequence, preferably a DNA sequence, that is used to mark the chromosome where it has integrated or may indicate a position where nucleic acid editing, such as by the CRSPR-CAS system, may occur. In this situation, the transgene does not have to include a gene that encodes a protein that may be expressed.

A gene of interest is a nucleic acid sequence that encodes a protein or other molecule, such as a RNA or targeting nucleic acid sequence, that is desirable for integration in a host cell. The gene of interest may include a 1, 2, 3, 4, 5, 6, 7, 8, 9, 10, or more genes of interest.

Genes of interest are useful for modulating the expression and/or activity of target biomolecules, either within the transduced cell or expressed for secretion outside of the transduced cell. Generally, genes of interest may be nucleic acids themselves or encode a polypeptide, a naturally-occurring binding partner of a target of interest, an antibody against a target of interest, a combination of antibodies against a target of interest and antibodies against other immune-related targets, an agonist or antagonist of a target of interest, a peptidomimetic of a target of interest, a peptidomimetic of a target of interest, a small RNA directed against or a mimic of a target of interest, and the like. Such modulators are well known in the art and include, for example, an antisense nucleic acid molecule, RNAi molecule, shRNA, mature miRNA, pre-miRNA, pri-miRNA, miRNA, anti-miRNA, or a miRNA binding site, or a variant thereof, or other small RNA molecule such as a Piwi RNA, triplex oligonucleotide, ribozyme, coding sequence for a target of interest. Such agents modulate the expression and/or activity of target biomolecules, which includes any decrease in expression or activity of the target biomolecule of at least about 30% to about 99% or more as compared to the expression or activity of the target biomolecule which has not been targeted by a modulating agent.

In one embodiment, the gene of interest is useful for expressing and/or enhancing the activity of a nucleic acid or protein of interest. For example, the gene of interest may encode a protein or other molecule the expression of which is desired in the host cell. Such protein-encoding nucleic acid sequences are not particularly limited and are selected based on the desired exogenous perturbation desired. Thus, the gene of interest includes any gene that the skilled practitioner desires to have integrated and/or expressed. For example, exogenous expression of proteins related to autoimmune, allergic, vaccination, immunotolerance, cancer immunotherapy, immune exhaustion, immunological memory, or immunological epitope responses may be used. The gene of interest encode a protein or be a nucleic acid that serves as a marker to identify cells of interest or transduced cells. The gene of interest may encode a protein that modifies a physical characteristic of the transduced cell, such as a protein that modifies size, growth, or eventual tissue composition. In another example, the gene of interest may encode a protein of commercial value that may be harvested. Generally, the gene of interest is operatively linked to other sequences that are useful for obtaining the desired expression of the gene of interest, such as transcriptional regulator sequences like inducible promoters, as described further below.

In another embodiment, the gene of interest is useful for inhibiting the expression and/or activity of a nucleic acid or protein of interest. For example, target biomolecule expression and/or activity, such as an RNA coding region, may be reduced or inhibited using inhibitory RNAs. An RNA coding region is a nucleic acid that may serve as a template for the synthesis of an RNA molecule, such as an siRNA. RNA interference (RNAi) is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see, for example, Coburn and Cullen (2002) J. Virol. 76:9225), thereby inhibiting expression of the target biomarker nucleic acid. In one embodiment, the RNA coding region is a DNA sequence. The ability to down-regulate a target gene has many therapeutic and research applications, including identifying the biological functions of particular genes. Moreover, such inhibition may be achieved in screening assays that take advantage of pooling techniques, whereby groups of about 2 to about 100, or more, or any number or range in between, of RNA inhibitory agents are transduced into cells of interest. Suitable inhibitory RNAs include, but are not limited to siRNAs, shRNAs, miRNAs, Piwis, dicer-substrate 27-mer duplexes, single-stranded interfering RNA, and the like.

siRNAs typically refer to a double-stranded interfering RNA. In addition to siRNA molecules, other interfering RNA molecules and RNA-like molecules may be used. Examples of other interfering RNA molecules that may to inhibit target biomolecules include, but are not limited to, short hairpin RNAs (shRNAs), single-stranded siRNAs, microRNAs (miRNAs), piwiRNA, dicer-substrate 27-mer duplexes, and variants thereof containing one or more chemically modified nucleotides, one or more non-nucleotides, one or more deoxyribonucleotides, and/or one or more non-phosphodiester linkages. Typically, all RNA or RNA-like molecules that may interact with transcripts RISC complexes and participate in RISC-related changes in gene expression may be referred to as interfering RNAs or "interfering RNA molecules.

Suitable interfering RNAs may readily be produced based on the well-known nucleotide sequences of target biomolecules. In various embodiments interfering RNAs that inhibit target biomolecules may comprise partially purified RNA, substantially pure RNA, synthetic RNA, recombinant produced RNA, as well as altered RNA that differs from naturally-occurring RNA by the addition, deletion, substitution, and/or alteration of one or more nucleotides. Such alterations may include, for example, addition of non-nucleotide material, such as to the end(s) of the interfering RNAs or to one or more internal nucleotides of the interfering RNAs, including modifications that make the interfering RNAs resistant to nuclease digestion. Such alterations result in sequences that are generally at least about 80%, or more, or even 100% identical to the sequence of the target biomolecule. When the gene to be down regulated is in a family of highly conserved genes, the sequence of the duplex region may be chosen with the aid of sequence comparison to target only the desired gene. On the other hand, if there is sufficient identity among a family of homologous genes within an organism, a duplex region may be designed that would down regulate a plurality of genes simultaneously.

The biological agent is bonded to the arms of the micelle, which in some embodiments can mean that the biological agent is physically entangled within at least some of the arms of one or more micelles. In other embodiments, the biological agent may be bound by electrostatic attraction to at least some of the arms of one or more micelles, and may also be physically entangled with the arms of the micelle.

For example, as shown schematically in FIG. 1(c), a strand of sgRNA can be added to sample of Cas9 protein, which forms an RNP that may be introduced into a substantially spherical micelle. The RNP becomes entangled and/or electrostatically bonded with at least some of the arms of the micelle to form a compound suitable for delivery of the RNP into a cell of a subject.

As further schematically illustrated in FIG. 1(c) and FIG. 2(b), in some embodiments the micelles complex with biological agents to form complexes referred to herein as micelleplexes. In some embodiments, micelleplexes offer more than four times higher transfection efficiency for pDNA compared to analogous polyplexes, with similarly low toxicity. Micelleplexes have higher cellular internalization, host a larger concentration of amines per package (potentially aiding endosomal escape), exhibiting a "beads-on-a-string" packaging motif mimicking the way cells wrap DNA around histones in chromatin and preserve the native B form of DNA structure upon packaging, which collectively aiding in payload accessibility for successful transgene expression. In some embodiments, the micelleplexes complex with RNP to form well-defined particles in PBS with moderate gene-editing efficiency, which could be further optimized for in vivo applications. In some embodiments, the micelleplexes complex with RNP to form large particles in water with superior gene-editing efficiency in vitro (twice as high as commercial vehicle Lipofectamine2000), offering promising for in vitro, ex vivo, and/or cell therapy applications.

In various embodiments, the micelleplexes can be characterized using static light scattering to determine micelleplex molecular weight and cargo loading. Cryo-TEM may be used to visualize micelles and micelleplexes directly and characterize morphology. For example, for pDNA delivery with diblock micelle, a plurality of micelles may be used to form the micelleplex, and in some embodiments more than 3 and up to 10 micelles or more may be used. In another example, for pDNA delivery with triblock micelles; the micelleplex may include about 2 to about 5, or about 2 to about 3 micelles per complex. For RNP delivery with micelleplexes formed in phosphate buffered saline, at certain concentrations a single micelle per micelleplex may be used with around 14 RNPs bind to micelle corona, and in ultrapure water multiple micelles and RNPs may aggregate to form a suitable micelleplex. In the present application the term aggregate means that the micelles and cargos not only bind to each other but may also bind with themselves to form larger particles. In various embodiments, the micelles associate with one another by, for example, cargo binding and bridging.

Figure 2:
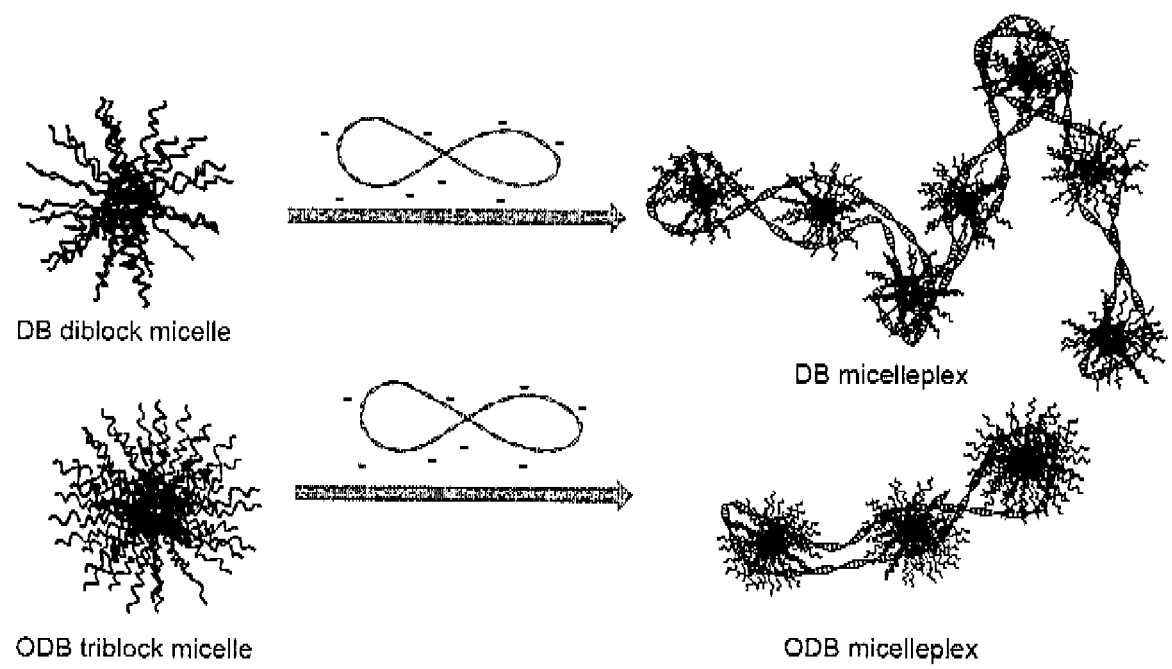
FIG. 2 is a schematic representation of a process in which a biological agent payload (pDNA) is bound to a micelle formed from the amphiphilic diblock copolymer DB and the amphiphilic triblock terpolymer ODB, which show how a biological payload bonds to multiple separate micelles to form a micelleplex.

Another example of micelleplex formation is shown in FIG. 2. FIGS. 2(a)-2(b) schematically illustrate micelles formed by the amphiphilic diblock copolymer DB and the amphiphilic triblock polymer ODB, and also illustrate how the micelles can form micelleplexes of differing size for binding to a selected biological agent. As shown in FIG. 2(b), in some embodiments a large biological agent can bond to more than one disassociated micelles to form a micelleplex.

In another aspect, the present disclosure is directed to compositions including the micelles described above which have been dispersed in an aqueous solution. In some embodiments, the micelles may be added to a liquid carrier and stored in liquid form until needed, or alternatively may be dried and introduced into and dispersed in the liquid carrier prior to administration to a subject.

In some embodiments the liquid carrier is a pharmaceutically acceptable carrier, which refers to a pharmaceutically-acceptable material, composition or vehicle for administration of a biological agent described herein. Pharmaceutically acceptable carriers include any and all solvents, dispersion media, coatings, antibacterial and antifungal agents, isotonic and absorption delaying agents, and the like which are compatible with the activity of the biological agent and are physiologically acceptable to the subject.

Some non-limiting examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, methylcellulose, ethyl cellulose, microcrystalline cellulose and cellulose acetate; powdered tragacanth; malt; gelatin; lubricating agents, such as magnesium stearate, sodium lauryl sulfate and talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol (PEG); esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; bulking agents, such as polypeptides and amino acids serum component, such as serum albumin, HDL and LDL; C2-C12 alcohols, such as ethanol; and other non-toxic compatible substances employed in pharmaceutical formulations.

Wetting agents, coloring agents, release agents, coating agents, sweetening agents, flavoring agents, perfuming agents, preservative and antioxidants can also be present in the formulation.

Pharmaceutically acceptable carriers can vary in a formulation described herein, depending on the administration route. The formulations described herein can be delivered to a cell or an organism via any administration mode known to a skilled practitioner. For example, the formulations described herein can be delivered in a systemic manner, via administration routes such as, but not limited to, simply applying the composition to an exterior surface of a cell, oral, intravenous, intramuscular, intraperitoneal, intradermal, and subcutaneous. In some embodiments, the compositions described herein are in a form that is suitable for injection. In other embodiments, the formulations described herein are formulated for oral administration.

In some embodiments, the liquid carrier for the micelles can be a solvent or dispersing medium, containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier ca be a buffered solution (e.g., PBS).

The formulations can also contain auxiliary substances such as wetting or emulsifying agents, pH buffering agents, gelling or viscosity enhancing additives, preservatives, colors, and the like, depending upon the route of administration and the preparation desired. Standard texts, such as "REMINGTON'S PHARMACEUTICAL SCIENCE," 17th edition, 1985, incorporated herein by reference, may be consulted to prepare suitable preparations. With respect to formulations described herein, however, any vehicle, diluent, or additive used should be biocompatible with the biological agents described herein.

The present disclosure is further directed to methods for delivering the biological agent bonded with the micelles and micelleplexes described above to a cell or to a subject. For example, after a composition including the micelles and biological agent payload bonded thereto is applied to the cell, the micelleplexes are delivered into the cell and the biological agent payload disassociates partially or completely from the micelles and a therapeutic amount of the biological agent takes effect therein.

In various embodiments, which are not intended to be limiting, the compositions may be administered to a cell in vitro by removing a cell from a subject, culturing the cells, applying to the cells a composition including a micelle and bonded biological agent to deliver a therapeutic amount of the biological agent into at least a portion of the cells, and optionally re-introducing the cell to the subject.

In another embodiment, a tissue cell therapy technique may be used in which a tissue sample is removed from a subject, a composition including a micelle and an bonded biological agent is applied to the tissue to deliver a therapeutic amount of the biological agent to modify a selected cell or region of the tissue, and the modified tissue is transplanted into the subject.

In another embodiment, a composition including a micelle and an associated biological agent is administered to a subject in vivo via direct injection into the bloodstream such that a therapeutic amount of the biological agent is delivered into desired target cells of the subject. In various embodiments, for in vivo administration a delivery device can be used to facilitate the administration of any composition described herein to a subject, e.g., a syringe, a dry powder injector, a nasal spray, a nebulizer, or an implant such as a microchip, e.g., for sustained-release or controlled release of any formulation described herein.

The devices of the present disclosure will now be further described in the following non-limiting examples.

EXAMPLES

Experimental Procedures

Materials and Instruments

All chemicals were purchased from Sigma Aldrich and used without further purification unless specified otherwise. 3-[4,5-Dimethylthiazol-2-yl]2,5-diphenyltetrazolium bromide (MTT) was purchased from Molecular Probes (Eugene, Oreg.). JetPEI (PolyPlus Transfections, Illkirch, France) and Lipofectamine2000 (Thermo Fisher Scientific, Waltham, Mass.) were used as positive controls for the biological transfection assays. Buffer and cell culture media were purchased from Gibco (Thermo Fisher Scientific, Waltham, Mass.) unless specified otherwise, including phosphate buffered saline (PBS) pH=7.4, Dulbecco's Modified Eagle Medium (DMEM, high glucose, Glutamax supplement), Reduced Serum Medium (Opti-MEM, Glutamax supplement), Antibiotic-Antimycotic (Anti/Anti; 100×), and Trypsin-EDTA (0.05%). Heat Inactivated Fetal Bovine Serum (HI FBS) was purchased from Atlanta Biologicals (Flowery Branch, Ga.). The HEK 293T cell line containing the Traffic Light Reporter (TLR) sequence was acquired as a gift from the laboratory of Professor Mark Osborn at the University of Minnesota.[1] Cas9 nuclease sNLS-SpCas9-sNLS was purchased from Aldevron (Fargo, N. Dak.). SgRNA (100 bp) was purchased from TriLink Biotechnologies (San Diego, Calif.), with the sequence of "GCACC-UAUAGAUUACUAUCCGUUUUAGAGCUA-GAAAUAGCAAGUUAAAAUAA GGCUAGUCCGUUAUCAAC-UUGAAAAAGUGGCACCGAGUCGGUGCUUUU" (the gray highlight is the 20 bp site-specific sequence). QuickExtract™ DNA Extraction Solution was purchased from Lucigen (Middleton, Wis.). AccuPrime™ Taq DNA Polymerase System for PCR amplification was purchased from Invitrogen (Thermo Fisher Scientific, Waltham, Mass.). Primers with the sequences of 5'-AGACCACCCCCATGTACAAA-3' and 5'-GGAAAACCCTTCCTGGTTTC-3' was ordered from Integrated DNA Technologies (IDT, Skokie, Ill.). Monarch® DNA Gel Extraction Kit was purchased from New England BioLabs (Ipswich, Mass.). Dynamic and static light scattering (DLS and SLS) were performed on a Brookhaven Instruments BI-200SM with a 637 nm laser. Zeta potentials were measured with a Malvern Zetasizer Nano ZS (Malvern Instrument Ltd., Worcestershire, United Kingdom). Cryogenic transmission electron microscopy (cryo-TEM) was performed on a FEI Tecnai G2 Spirit BioTWIN (Hillsboro, Oreg.) microscope equipped with an Eagle 4-megapixel CCD camera (2048×2048 pixels), and a single-tilt cryo holder was used. Lacy carbon/Formvar grids were treated by PELCO easiGlow glow discharge cleaning system immediately before use.

Vitrified cryo-TEM samples were prepared by using a FEI Vitrobot. The MTT cytotoxicity assay plates were analyzed with a Biotek Synergy H1 plate reader (BioTek Instruments, Winooski, Vt.). Flow cytometry experiments were carried out on BD Fortessa H0081 flow cytometer with 100 mW Violet (405 nm), Blue (488 nm) and Yellow-Green (561 nm) lasers. Flow cytometry data were analyzed using FlowJo software (V10) from FlowJo (Ashland, Oreg.). PCR amplifications were performed on C1000 Touch™ Thermal Cycler from Bio-Rad (Hercules, Calif.).

Micelle Preparation

PDMAEMA-b-PnBMA (DB) and PEO-b-PDMAEMA-b-PnBMA (ODB) polymers were synthesized and characterized according to our previous report. DB micelles were prepared by directly dissolving DB polymers in water at 1 mg/mL following procedures described by Sprouse et al. ODB(2) and ODB(5) micelles were prepared through the cosolvent method, with polymers first dissolved in DMF (1 wt %) followed by adding MOPS buffer at pH 7 and 100 mM ionic strength, and then dialyzed against PBS buffer, as described by Jiang et al. ODB(10) micelles were prepared by the cosolvent method. First, 50 mg of the ODB(10) polymer was dissolved in 1.0 mL of DMF and stirred for 15 min. Then, a syringe pump was used to add 1.0 mL of DI water at a rate of 12 mL/h while stirring the solution. The sample was transferred to a 1 kDa MWCO dialysis bag and dialyzed against either 1.5 L buffer (20 mM, pH 7.4, ionic strength 150 mM NaCl) or 1.5 L Millipore water to acquire ODB(10) micelles in PBS and water, respectively. The samples were diluted to the desired concentrations and stored at −5° C. in a refrigerator.

Micelleplex Formation

Micelleplexes in PBS (20 mM, pH 7.4, ionic strength 154 mM NaCl) and water were prepared at polymer:RNP molar ratios of 2.5:1 and 5:1 right before use. To formulate the RNP solutions, the sgRNA (0.065 mg/mL in PBS, 0.039 mg/mL in water) solution was added into a solution containing Cas9 protein (0.32 mg/mL in PBS, 0.19 mg/mL in water) at equivalent volume aliquots to obtain the final RNP solution that contained a 1:1 Cas9:sgRNA molar ratio. The RNP solution was allowed to bind for 15 min at room temperature prior to micelleplex formulation. Next, the same volumes of micelle solutions at appropriate concentrations were each added to RNP solutions to achieve polymer:RNP molar ratio 2.5:1 and 5:1, respectively. The micelleplex solutions were allowed to equilibrate at room temperature for 1 hour before use.

High-Throughput Dynamic Light Scattering (DLS)

The tubes used for DLS analysis were all thoroughly precleaned with ultrapure water and ethanol, which was filtered with 0.2 μm filters prior to cleaning, covered with aluminum foil, and air dried overnight before use. Micelleplexes were formed according to the procedure described in Micelleplex Formation section. Micelle solution and sgRNA solution were prefiltered with 0.2 μm filters. Cas9 protein was used directly as it was found to adhere to the filter membrane during filtration process. To avoid potential alteration in the micelleplex structure due to filtration, the micelleplex solutions were not filtered after formation.

For high-throughput DLS, samples were transferred into a glass-bottomed 96-well DLS plate (Greiner Bio One GmbH, SensoPlate, 655892) using a multi-channel pipette. The well plate was placed in the DynaPro Plate Reader III (Wyatt Technology, Santa Barbara, Calif.) and equilibrated at 23° C. Wells containing samples of interest were analyzed using automated measurements. For each measurement, five acquisitions were recorded with an acquisition time of 5 seconds each. The resulting auto-correlation function was fitted using the cumulants model to yield the hydrodynamic radius and dispersity.

Cell Culture

Engineered HEK 293T TLR cell line was cultured in high glucose DMEM with 10% HI FBS and 1% Antibiotic/Antimicrobic. The incubator was set at humidified atmosphere under 37° C. with 5% $CO_2$. Cell confluency was monitored, and cells were passaged as needed.

Gene-Editing Efficiency Measurement by High-Throughput Fluorescence Microscopy

The combination of image cytometry, which acquires fluorescence imaging of HEK cells in each transfection condition, together with automated image analysis using CellProfiler, a software package that facilitates rapid and accurate image analysis,[4,5] enabled high-content screening of the gene editing efficiency and the selection of best performing micelleplex candidate. Although image cytometry is a staple in high-throughput screening campaigns in pharmaceutical research, it is underexplored as a tool to select effective polymeric vehicles for cargo delivery, and only a limited report was found on optimizing lipid delivery vehicles.[10] HEK 293T TLR cells were plated in 48 well-plate (Corning Costar #3548) at a density of 50,000 cells/mL. Micelleplexes were formed as described in Micelleplex Formation section. Micelleplexes formed in water were used directly, micelleplex formed in PBS were further diluted with PBS before transfection to achieve final concentrations of Cas9 protein and sgRNA of 0.049 mg/mL and 0.0097 mg/mL, respectively, in both water and PBS conditions. DLS showed that the size of the micelleplexes formed in PBS do not change after further PBS dilution. 240 μL of Opti-MEM was added to 120 μL of each micelleplexes solutions right before transfection. The final dose of Cas9 protein and sgRNA were 2.4 μg/well and 0.49 μg/well, respectively. Four hours after transfection, 0.5 mL of fresh DMEM containing 10% FBS was added to each well. The micelleplexes solution was aspirated 24 h after transfection, and cell culture media was replaced by fresh DMEM containing 10% FBS. Cells were visualized using live-cell microscopy 48 h after transfection under the following procedures.

Cells were stained with NucBlue Live ReadyProbes Reagent (Invitrogen, Thermo Fisher Scientific, Waltham, Mass., catalog #R37605) by adding one drop of NucBlue stain per well and incubating for 20 minutes. Subsequently, the cell culture media was replaced with FluorBrite (Thermo Fisher Scientific, Waltham, Mass. catalog #A1896701) for optimal visualization. A Zeiss inverted microscope, Axios Observer (Oberkochen, Germany) was used in wide field mode in combination with a fully enclosed chamber heated to 37° C., supplied with 5% $CO_2$ and humidified with deionized water. The well plate was moved over a 10× objective using a motorized stage and 4-15 images were acquired per sample. Image acquisition was performed in two fluorescence channels: Hoechst 33342 and mCherry with uniform exposure time and shading corrections applied throughout the well plate.

High Content Image Analysis

Cell Profiler (Broad Institute, MA), an open source software platform was used to estimate the proportion of mCherry positive cells. Our pipeline was developed by using the module "Cell/particle counting and scoring the percentage of stained objects" as a starting point and modifying it according to the needs of our dataset. Corrections for uneven illumination (or background subtraction) were performed using the Correct Illumination Calculate module in both the Hoechst and the mCherry channels. Cell outlines were identified using the Identify Secondary Objects module by assuming a distance of 20 pixels from the nucleus to the outer edge of the cell. Our algorithm allowed for clumped cells to be recognized and separated and for the dividing lines between adjacent cells to be identified. Cells at the edges of the image were discarded and not included in the analysis. Finally, cells were classified into mCherry-positive or negative by measuring mCherry intensities and using 0.05 as the threshold for separation. The Cell Profiler pipeline will be shared to readers based on inquiries. The entire cycle of image acquisition, image processing, statistical analysis, and candidate selection was completed within 5-6 hours for all formulations. This live cell imaging and automated analysis technique provides a rapid protocol for formulation screening and discovery as it eliminates the need for cell trypsinization and washing steps, thus, increasing the throughput, parallelizing the workflow, and allowing promising formulations to be identified rapidly.

Gel Electrophoresis

The ability of the micelles to bind with Cas9 RNP and form micelleplexes was qualitatively determined by gel electrophoresis. Initially, RNPs were prepared by adding sgRNA (0.10 mg/mL) to Cas9 protein (0.50 mg/mL) at 5 μL of each solution to achieve 1:1 Cas9:sgRNA molar ratio. After incubation for 15 min, a 10 μL aliquot of the micelle solution at the appropriate concentration was added to 10 μL of RNP samples to achieve polymer:RNP molar ratios of 2.5:1 and 5:1, respectively. Then, 2 μL of loading buffer was added and 20 μL of each sample was loaded into wells in a 2.0% agarose gel containing 1.5 g of ethidium bromide/mL TAE buffer. The electrophoresis was carried out for 90 min at 80 V. The gel is visualized using a standard UV transilluminator.

Zeta Potential

The samples were prepared as described in Micelleplex Formation section and were kept in a folded capillary cell equipped with gold plated electrodes. The mobility was measured with a Malvern Zetasizer Nano ZS. The zeta potential was calculated from the measured electrophoretic mobility using the Smoluchowski equation.

Multiangle DLS Analysis

ODB(10) sample preparation followed the same procedures described in High-Throughput DLS section. All measurements were carried out at 23° C. The correlation function for each sample was collected at 5 angles ranging from 60° to 120°, and data were collected for 10 min at each angle. The size distributions were assessed by applying the REPES algorithm$_{12}$ to the correlation function obtained at 90°. The correlation functions of each sample were fitted to a cumulant model. The fitting procedures were previously detailed.

Static Light Scattering (SLS) and Estimation of Binding Fraction

ODB (10) samples were prepared following the same procedure in PBS at polymer:RNP=2.5:1 molar feed ratio as described above in Micelleplex Formation section, and were diluted to three lower concentrations with prefiltered PBS buffer. The micelle dn/dc was previously measured as 0.14 mL/g. The dn/dc value of the Cas9 protein solution was estimated as 0.182 mg/mL, based on previously published similar protein dn/dc values, and the dn/dc value of the RNA solution was 0.171 mg/mL, based on previous literature. The dn/dc value of the micelleplex solution was estimated as 0.161 mL/g based on the weight fraction of its components:

$$dn/dc_{micelleplex} = \frac{dn/dc_{Cas9} * MW_{Cas9} + dn/dc_{sgRNA} * MW_{sgRNA} + dn/dc_{micelle} * MW_{micelle}}{MW_{Cas9} + MW_{sgRNa} + MW_{micelle}} \quad (1)$$

Toluene was used for calibration ($R_\theta$=1.363×10$^{-5}$ cm$^{-1}$). Berry analysis was used to calculate apparent weight-averaged molar mass $M_{w,apparent}$, radius of gyration $R_g$, and second virial coefficient A2.

Figure 6:
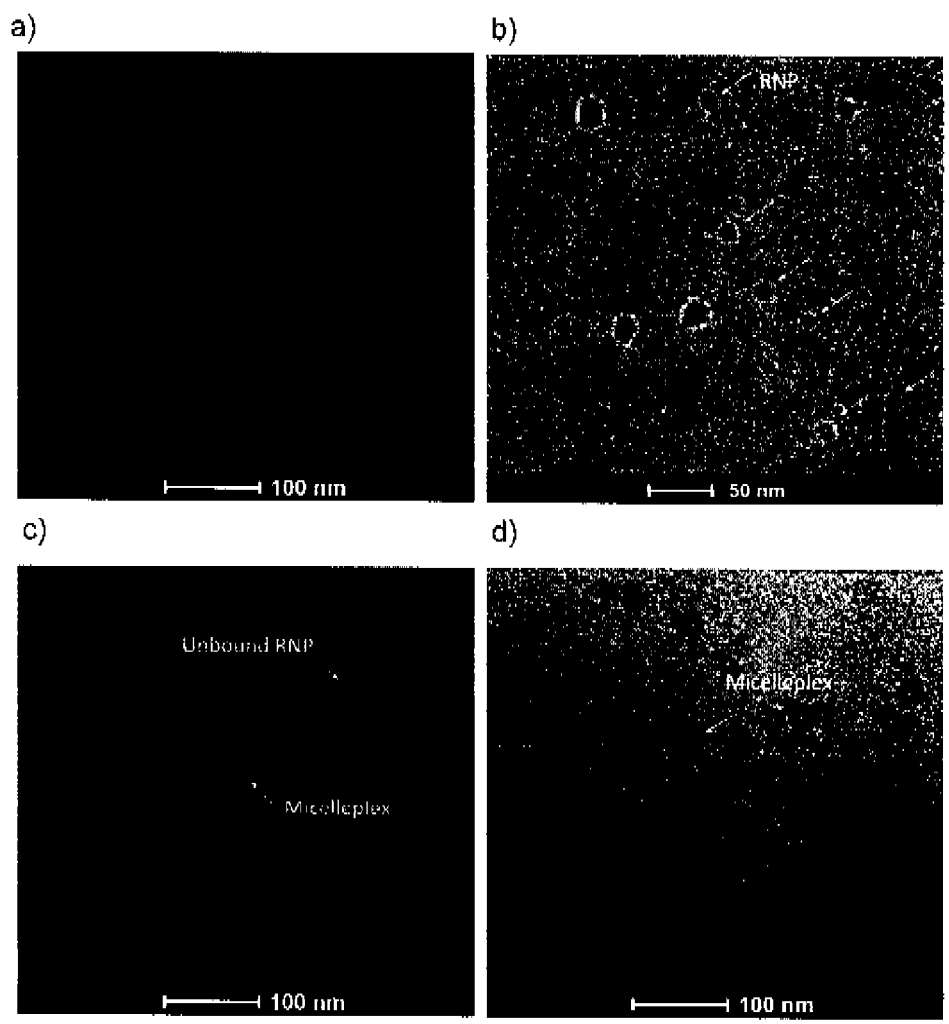
FIGS. 6(a)-(d) are representative cryo-TEM images in PBS of (a) ODB(10) micelles, (b) RNPs, (c) micelleplexes at ODB(10) polymer:RNP molar formulation ratio 2.5:1, and (d) micelleplexes at ODB(10) polymer:RNP molar formulation ratio 5:1.

The $M_{w,apparent}$ of the ODB(10) micelleplexes (5.2×10$^6$ g/mol) as measured by SLS represents the weight-average of all components in the solution. At 2.5:1 polymer:RNP molar feed ratio, which is 1:25 micelle:RNP molar feed ratio, RNP is in large excess in the formulation. As the cryo-TEM image in FIG. 6(c) shows, the solution contains both free RNPs and micelleplexes containing single micelles and multiple bound RNP decorating the micelle corona. Therefore, the $M_{w,apparent}$ of the complexes can be expressed as $$M_{w,apparent} = \frac{n_{complex}M^2_{w,comlex} + n_{RNP}M^2_{w,RNP}}{n_{complex}M_{w,comlex} + n_{RNP}M_{w,RNP}} \quad (2)$$

where $n_{complex}$ and $n_{RNP}$ are molar concentrations of complexes and excess free RNP, respectively. $M_{w,complex}$ and $M_{w,RNP}$ are the molar mass of complex and RNP. $M_{w,RNP}$ is calculated as 1.94×10$^5$ g/mol based on the molar mass of Cas9 protein and sgRNA.

With the assumption that all complexes are identical, the $M_{w,complex}$ can be calculated as $$M_{w,complex} = M_{w,micelle} + aM_{w,RNP} \quad (3)$$

where a is the number of RNP per micelle in complexes and $M_{w,micelle}$ is the molar mass of micelle (3.9×10$^6$ g/mol). Since the mass balance of RNP and micelles have to be satisfied, as the following:

$$n_{micelle} = n_{complex} \quad (4)$$

$$n_{RNP,total} = n_{RNP} + an_{complex} \quad (5)$$

where $n_{micelle}$ and $n_{RNP,total}$ are known molar concentrations of micelles and all RNPs in the solution.

By substituting $M_{w,complex}$ and $n_{complex}$ using Equations S2 and S3, and solving Equations S1 and S4 together, a was obtained as 14 and $n_{RNP}$ was found to be 44% of $n_{RNP,total}$.

Cryogenic Transmission Electron Microscopy (Cryo-TEM)

The morphologies of the ODB(10) micelles and micelleplexes in aqueous buffer were visualized by cryo-TEM. For each specimen, 3-4 µL of micelle or micelleplex solution was loaded onto a carbon-coated and lacey film-supported copper TEM grid in the climate chamber of a FEI Vitrobot Mark III vitrification robot. The climate chamber was held at 26° C. with saturated water vapor. The loaded grid was blotted and then plunged into liquid ethane that was cooled by liquid $N_2$. Vitrified samples were kept under liquid $N_2$ before being imaged. Images were taken under focus for adequate phase contrast.

In Vitro Cell Transfection with Micelleplexes

The quantification of the gene editing efficiency of the Cas9 RNP delivered by the ODB(10) polymer micelles was carried out via a Traffic Light Reporter (TLR) assay. HEK 293T TLR cells were plated in a 24-well plate at a density of 50,000 cells/well. After 24 hours, micelleplexes were prepared at Cas9:sgRNA:polymer molar ratios of 1:1:2.5 and 1:1:5.

Figure 16:
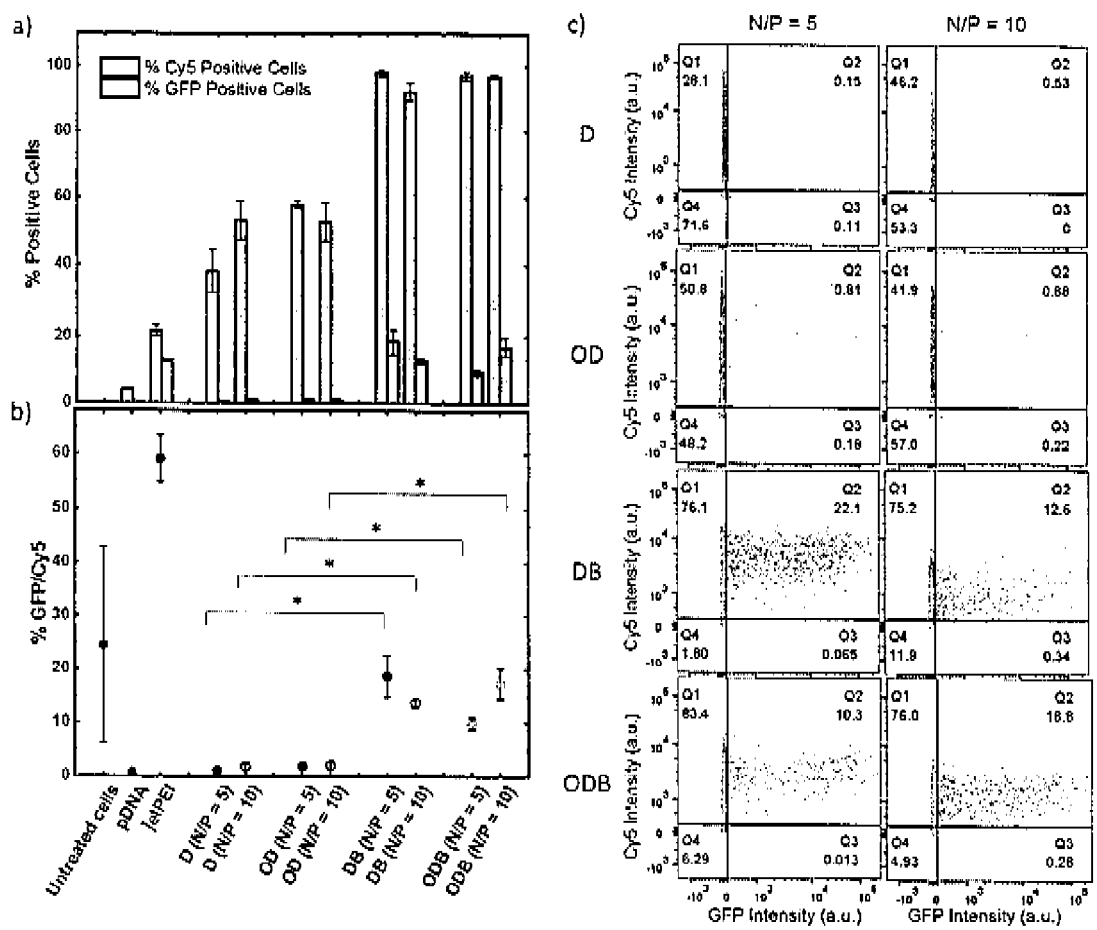
FIGS. 16(a)-(c) are plots of HeLa cell internalization assays with complexes formed with Cy5-labeled pDNA. Percent $Cy5_+$ cells and percent $GFP_+$ cells were analyzed 24 h after transfection (n=3). Data are presented as mean standard deviation.

Micelleplexes were formed in PBS according to a similar procedure as described in Micelleplex Formation section: the RNP solution was prepared by mixing 52 µL of sgRNA (0.065 mg/mL) in PBS with 52 µL of Cas9 protein (0.32 mg/mL) in PBS. The mixture was allowed to bind at room temperature for 15 min. ODB(10) micelle solutions (104 µL) at 0.16 mg/mL and 0.32 mg/mL in PBS was added to the RNP solution to achieve 2.5:1 and 5:1 polymer: RNP molar feed ratios, respectively. The mixtures were allowed to bind at room temperature for 1 h for complexation. Next, 143 µL of PBS was added to the micelleplex solution to dilute the system. DLS measurements showed that micelleplex size remained the same after dilution (FIG. 16).

The total volume of the micelleplex solution was 350 µL, and the final concentrations of Cas9 protein and sgRNA in micelleplex solution were 0.049 mg/mL and 0.0097 mg/mL, respectively.

Micelleplexes were formed in water according to the following procedure: the RNP solution was prepared by mixing 88 µL of sgRNA (0.039 mg/mL) in water with 88 µL of Cas9 protein (0.19 mg/mL) in water. The mixture was allowed to bind at room temperature for 15 min. ODB(10) micelle solutions (175 µL) in water were prepared at 0.096 mg/mL and 0.192 mg/mL and were added to the RNP solutions to achieve polymer:RNP molar ratios of 2.5:1 and 5:1, respectively. The solution mixtures were allowed to complex at room temperature for 1 hr. The total volume of the micelleplex solution was 350 µL, and the final concentrations of Cas9 protein and sgRNA were 0.049 mg/mL and 0.0097 mg/mL, respectively.

Twice the volume (700 µL) of Opti-MEM was then added to each of the micelleplex solutions immediately prior to transfection. In the plate of cells, each well was aspirated to remove media, and 300 µL of the micelleplex solution was added to each well. Four hours after transfection, 1 mL of DMEM containing 10% FBS was added to each well. Twenty-four hours after initial transfection, the media was aspirated from each well and replaced with fresh DMEM containing 10% FBS. The cells were harvested 48 hr after transfection for gene-editing analysis.

Traffic Light Reporter (TLR) Assay

Figure 17:
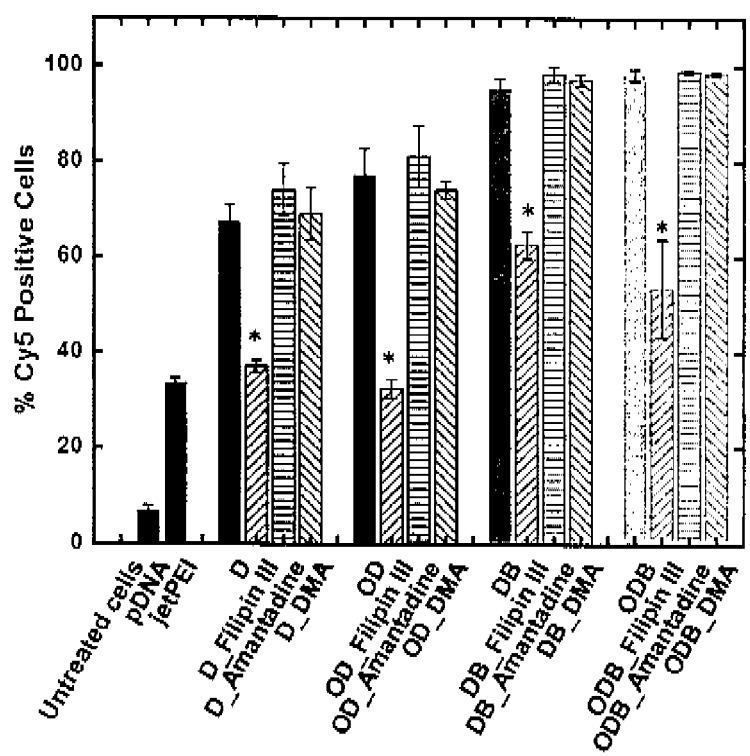
FIG. 17 is a plot of endocytosis pathway inhibition assays with HeLa cells. Filipin III was used to inhibit caveolae, amantadine was used to inhibit clathrin, and 5-(N,N-dimethyl) amiloride (DMA) was used to inhibit macropinocytosis. Statistically significant differences compared to uninhibited samples are denoted by "*" ($p<0.05$). Data are presented as mean standard deviation (n=3).

A TLR assay with HEK 293T cells was used to estimate the fraction of cells positive for genome editing with the ODB(10) micelleplexes and controls. Cells were transfected as described above. The fraction of cells expressing mCherry was determined by flow cytometry analysis. Live cells were identified using Calcein Violet AM viability dye. The flow cytometry analysis was performed using a BD LSRFortessa from BD Biosciences (San Jose, Calif.). At least 10,000 single cell events were collected for each sample and representative of the gating are shown in FIG. 17.

TIDE Assay

DNA of the cells transfected with ODB(10) micelleplexes and controls below were extracted with QuickExtract™ DNA Extraction Solution and PCR amplified use AccuPrime™ Taq DNA Polymerase System following the manufacturer's protocols.

| | | OD polyplexes | |
|---|---|---|---|
| | OD polymer | Free polymer | Polyplex |
| $D_t$ (× $10^{11}$ $m^2$/s) by PFG-NMR | 3.4 | 3.9 | 0.80 |
| $R_h$ (nm) by PFG-NMR | 6.8 | 5.8 | 28.4 |
| $D_t$ (× $10^{11}$ $m^2$/s) by DLS | 5.0 | 5.0 | 0.46 |
| $R_h$ (nm) by DLS | 4.6 | 4.6 | 50 |

PCR products were purified with 1 wt. % agarose gel electrophoresis. The corresponding band was cut and purified with a Monarch® DNA Gel Extraction Kit to harvest the DNA, following manufacture's protocols. The DNA samples together with the primers were sent out to GeneWiz® for sequencing. Data was analyzed by TIDE web tool.

MTT Assay

HEK 293T TLR cells were plated in a 24-well plate at a density of 50,000 cells/well. ODB(10) micelle solutions at various concentrations were prepared in Opti-MEM media. The wells were aspirated and replaced with 300 µL aliquots of the formulations. After 4 h, 1 mL of DMEM with 10% HI FBS was added to each well. Twenty-four hours post-treatment, the media was aspirated and replaced with fresh DMEM containing 10% HI FBS. The MTT assay was conducted 48 h post-transfection. MTT reagent 100 µL (5 mg/mL) in PBS was added to each well and incubated for 2 hr. Subsequently, the media was aspirated and DMSO 500 µL was added to each well. Next, samples were transferred to a fresh plate and absorbance was measured at 570 nm using a Synergy H1 Hybrid Reader (BioTek, Winooski, Vt.).

Example 1—Delivery of mRNA

Complex Formation

A PDMAEMA-b-PnBMA (DB) diblock copolymer and three PEO-b-PDMAEMA-b-PnBMA (ODB) triblock polymers were synthesized via reversible-addition-fragmentation chain transfer (RAFT) polymerization to acquire uniform chain lengths. The polymers were characterized according to published procedures (Table 1).

TABLE 1

Synthetic Block Polymer Characterization

| | Polymer | DB | ODB (2) | ODB (5) | ODB (10) |
|---|---|---|---|---|---|
| Block length (kDa) | PEO | — | 2 | 5 | 10 |
| | PDMAEMA | 27 | 27 | 27 | 28 |
| | PnBMA | 14 | 24 | 25 | 24 |
| | Đ | $1.10^a$ | $1.12^b$ | $1.18^b$ | $1.14^b$ |

The DB and ODB polymers self-assembled to form spherical micelles exhibiting core-shell or core-shell-corona architectures, respectively (see FIG. 1). The PnBMA hydrophobic chain length was chosen such that after micelle formation, the cores are kinetically constrained from chain exchange at room temperature due to the strong hydrophobic nature of PnBMA and long block length. Thus, the micelles were stable with respect to size and shape.

The Cas9 protein used was sNLS-spCas9-sNLS, which contains nuclear localization signals on both ends of the protein to promote efficient nuclear trafficking once delivered inside the cell. When forming micelleplexes, sgRNA was first added to Cas9 protein at a 1:1 molar ratio and allowed to complex for 15 min. Micelle solutions were then added to the RNP solution and allowed to further complex for 1 hr. The systems were examined at a polymer:RNP molar formulation ratio of both 2.5:1 and 5:1. All four micelle variants were designed to contain the same cationic (PDMAEMA) block chemistry and lengths, thus, at a certain polymer:RNP molar ratio, the molar ratio of RNP to amine groups are consistent across all four micelleplex formulations.

Micelleplex Formulation and High-Content Screening

Figure 3:
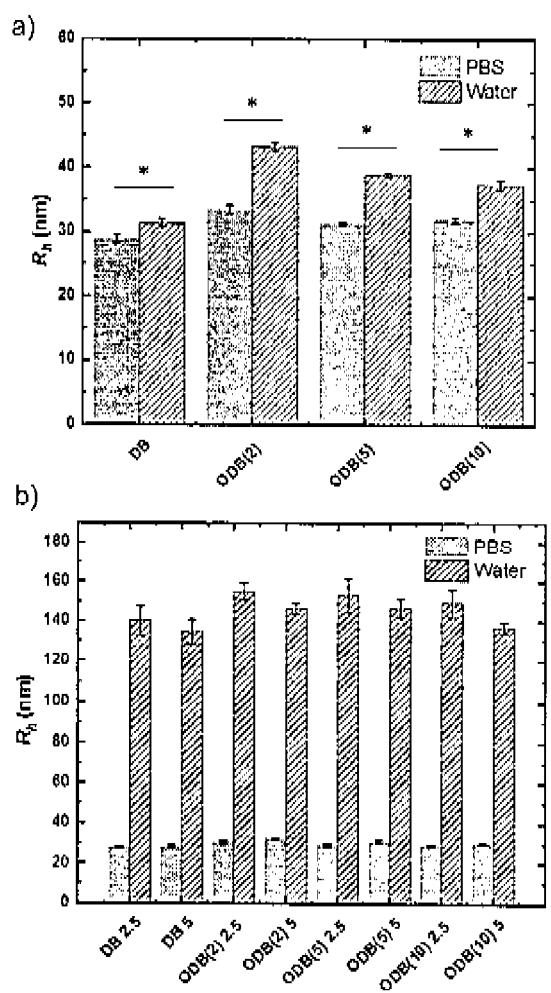
FIGS. 3(a)-3(b) are plots showing micelle and micelleplex (with CRISPR-Cas9 RNP) sizes formulated in water and PBS as measured by high-throughput DLS. Each sample was measured with 5 acquisitions (n=5), 5 s each, with data represents mean standard deviation.

Micelleplexes were formulated in two common solvents for biological delivery studies, phosphate buffer saline (PBS) and water, and characterized for size via high-throughput DLS (FIG. 3). The four bare micelle species without RNP were found to have similar hydrodynamic radii ($R_h$), between 28-34 nm in PBS and slightly larger sizes of 30-44 nm in water, presumably due to the elongated cationic corona under low ionic strength, in agreement with previous work on polycation solution physics. While the PEO block indeed adds some hydrodynamic volume, the PEO length did not appear to influence the hydrodynamic radius of the micelles under these conditions, as the aggregation number of the micelles decreases with increasing corona chain length. All micelleplex formulations were found to have similar sizes in each respective solution after formulation regardless of micelle architecture. Micelleplexes formulated in PBS had $R_h$ values around 30 nm, (similar to the bare micelles), indicating that the RNPs might nestle into the cationic block. In comparison, larger particles with $R_h$ of around 135-155 nm were formed in water. To further understand the mechanistic phenomena associated with these differences, these results were examined in detail (vide infra).

An engineered HEK 293T cell line with an imbedded traffic light reporter (TLR) system was utilized as the model cell line to screen delivery efficiency and genome-editing. The 20 bp sgRNA has been designed to target binding of the Cas9 nuclease to a genomic region upstream of an out-of-frame mCherry gene engineered into the HEK 293T genome. If the RNP is successfully delivered to the nucleus (and binds this genomic site), a double strand DNA break (DSB) will occur at the target locus and then be repaired via nonhomologous end-joining (NHEJ), a native cellular mechanism that quickly ligates the broken ends through insertion or deletion (indel) base mutations. The indels caused frame shifts to occur in the downstream mCherry gene; a fraction of those indels led to the correct frame shift to upregulate mCherry expression (red fluorescence), which can be visualized and quantified under fluorescence microscopy. It should be noted that the percentage of mCherry-positive (mCherry$_+$) cells is lower than the percentage of total edited cells because not all frame shifts induce mCherry production. Nonetheless, this is a facile method for high content screening to speedily and efficiently identify the candidates that displayed the best editing outcomes, as measured by mCherry expression.

Using this cell line, we compared the gene-editing performance of different micelleplex formulations across two solvent environments (PBS and water), 4 micelle compositions, and 2 molar ratios, giving rise to 16 possible candidates. Forty-eight hours after transfection of the HEK 293T TLR cells with the micelleplex formulations and controls, the cell nuclei were stained with Hoechst and microscopy acquisition was performed. Finally, an image analysis pipeline developed in CellProfiler was used to compute the ratio of mCherry$_+$ cells to the total number of nuclei in every image.

Figure 4:
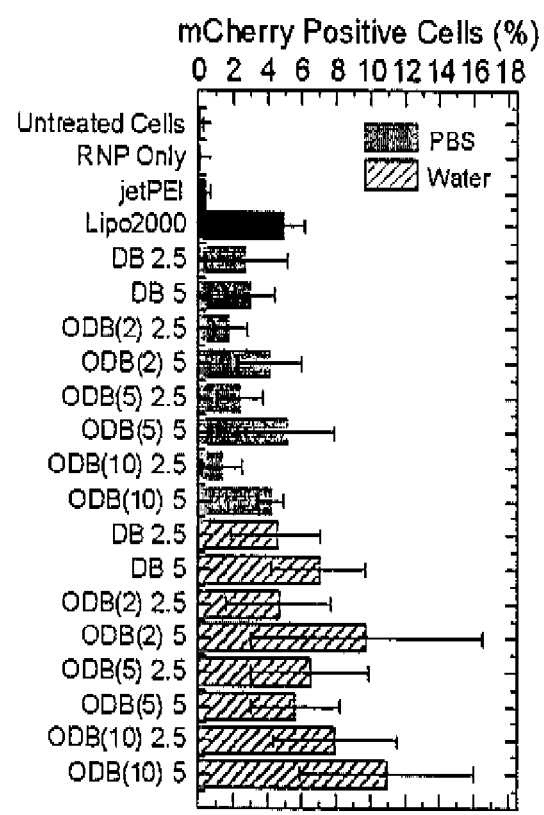
FIG. 4 is a plot showing summarized results of % mCherry+ cells. Data are presented as mean of % mCherry+ cells in each image standard deviation. The asterisk "*" indicates statistically higher compared to Lipofectamine2000 ($p<0.05$). Data were analyzed by one-way ANOVA followed by a post hoc Tukey test.

As shown in FIG. 4, in general, all micelleplex formulations promoted mCherry expression higher than the jetPEI control and many formulations appeared to match the efficiency promoted by Lipofectamine 2000 (5% mCherry$_+$) or even higher levels (Avg. 2-11% mCherry$_+$). Since high mCherry expression is indicative of high editing efficiency, it was concluded that the formulations in water reached higher editing efficiencies (Avg. 5-11% mCherry$_+$) than formulations in PBS (Avg. 2-5% mCherry$_+$). Higher delivery efficiency in water is potentially a consequence of the larger complex size and higher settling velocities, which is further discussed below. Moreover, all micelleplexes formed in water exhibited similar or higher editing efficiency compared to Lipofectamine 2000, regardless of the micelle architecture. Using this process, the ODB(10) variant, which promoted statistically higher mCherry expression than Lipofectamine, was identified as the best candidate vehicle and the focus of extensive biophysical characterization.

Quantitative Characterization of ODB(10) Micelleplexes

Figure 5:
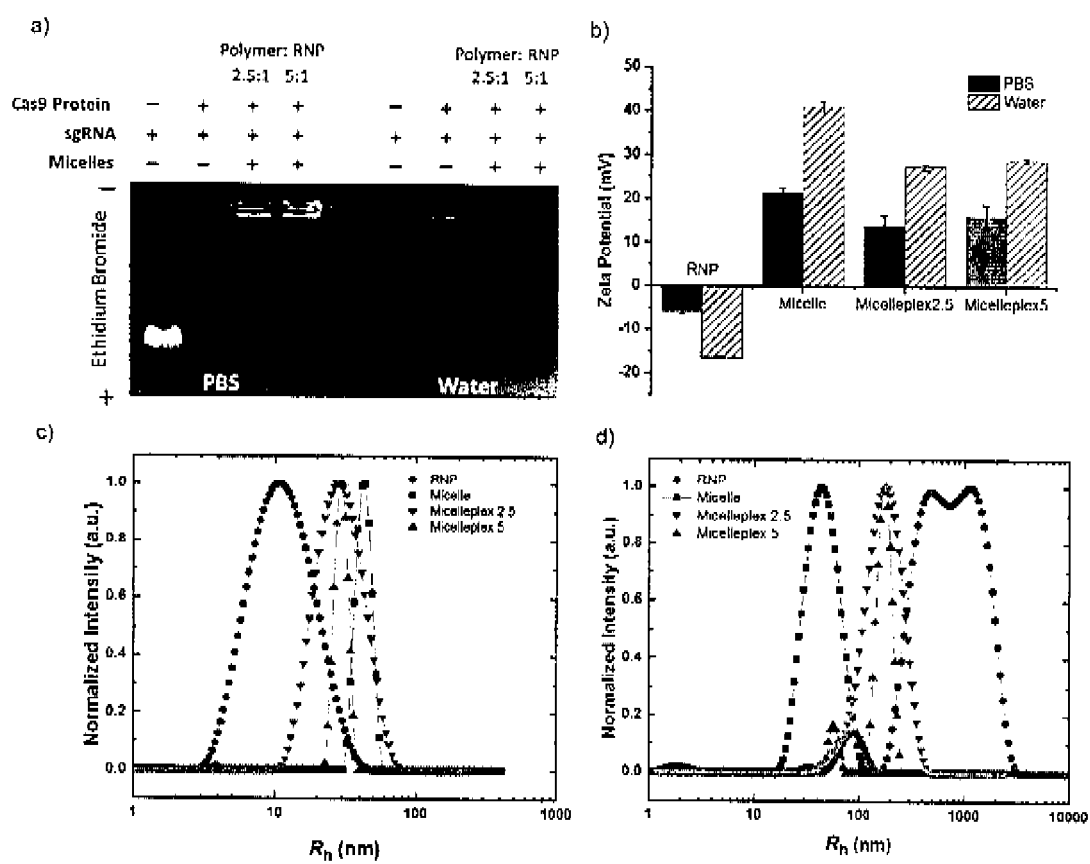
FIG. 5(a) is a gel electrophoresis assay of sgRNA only, RNP, and micelleplexes at ODB(10) polymer:RNP molar ratio of 2.5:1 and 5:1, in both PBS and water conditions.
FIG. 5(b) is a plot of the zeta potential of RNP, micelles, and micelleplexes in PBS and water (n=3).
FIGS. 5(c)-(d) are plots of the hydrodynamic radii ($R_h$) of RNP, ODB(10) micelles, and their micelleplexes by DLS in PBS c) and in water d). Size distribution were acquired by applying the REPES algorithm to the correlation function obtained at 90°.

Micelleplex complexation was characterized by gel electrophoresis (FIG. 5($a$)). In both PBS and water, sgRNA migrates towards the anode due to its overall negative charge. After complexation with Cas9 protein, the RNP migration in PBS was less than that of sgRNA, indicating stable binding of the sgRNA to the Cas9 protein, which maintained an overall negative charge. However, in water, the RNP migration was completely impeded, which potentially denoted the formation of large RNP aggregates. Upon addition of micelles, the complete lack of RNP migration in both PBS and water suggested the formation of micelleplexes. Zeta potential analysis (FIG. 5($b$)) showed that overall, particles had higher absolute values of Zeta potential in water compared to PBS, due to low solution ionic strength. In both solvent conditions, the RNP sample exhibited a negative Zeta potential due to the overhanging negative charge on the sgRNA, which leads to electrostatic interaction with the cationic micelle brush. As expected, the Zeta potential of the micelles was highly positive and decreased slightly after micelleplex formation.

To quantitatively analyze and compare the size, composition, morphology, and RNP loading of the ODB(10) micelleplexes in PBS and water, multi-angle DLS and cryo-TEM characterizations were performed. The DLS results revealed that in PBS, RNP has a radius of hydration ($R_h$) of around 9 nm (FIG. 5($c$)), which agrees with the single RNP size in a previous report. The micelleplexes formed in PBS have $R_h$ values of 26 nm ($\mu_2/\Gamma^2=0.13$) and 27 nm ($\mu_2/\Gamma^2=0.06$) at ODB(10) polymer:RNP molar ratio 2.5:1 and 5:1, respectively, slightly smaller than the uncomplexed micelles (FIG. 5($c$), Table 2).

TABLE 2

Hydrodynamic Radii and Dispersity of RNP, Micelles and Micelleplexes

| Condition | Sample | $R_h$ (nm) | $\mu_2/\Gamma^2$ |
|---|---|---|---|
| PBS | RNP | 9 | 0.34 |
|  | Micelle | 30 | 0.30 |
|  | Micelleplex 2.5 | 26 | 0.13 |
|  | Micelleplex 5 | 27 | 0.06 |
| Water | RNP | 506 | 0.6 |
|  | Micelle | 40 | 0.22 |
|  | Micelleplex .2.5 | 155 | 0.19 |
|  | Micelleplex 5 | 149 | 0.26 |

This result provides evidence that the micelleplexes in PBS consist of single micelles, and that the binding between the PDMAEMA cationic midblock and RNP leads to a slight contraction of the micelle corona. This observation of micelle compaction agrees with previous literature showing that the complexation of oppositely charged polyelectrolytes leads to micelle corona contraction. By comparison, the RNPs have large particle sizes ($R_h$>500 nm) in water (FIG. 5(d)), presumably due to the collective aggregation of multiple RNPs under low ionic strength and/or electrostatic bridging of the cationic Cas9 protein with the anionic sgRNA. Interestingly, the formation of micelleplexes helped to reduce the degree of RNP aggregation by reducing the micelleplex $R_h$ to around 150 nm. The above phenomena indicated different mechanisms of micelleplex formation under different buffering conditions. In PBS, the single micelles appear to act as the "template host" to RNPs for micelleplex formation, where individual RNPs bind within the ionic brush layer. In water, however, the RNPs may form loose aggregates, thus serving as the "template host" and micelles appear to break up the loose aggregates binding around the proteins and interacting with RNPs to form larger multi-micelle complexes, which could significantly influence particle settling kinetics (and thus cellular contact) in adherent cell transfection experiments.

Figure 7:
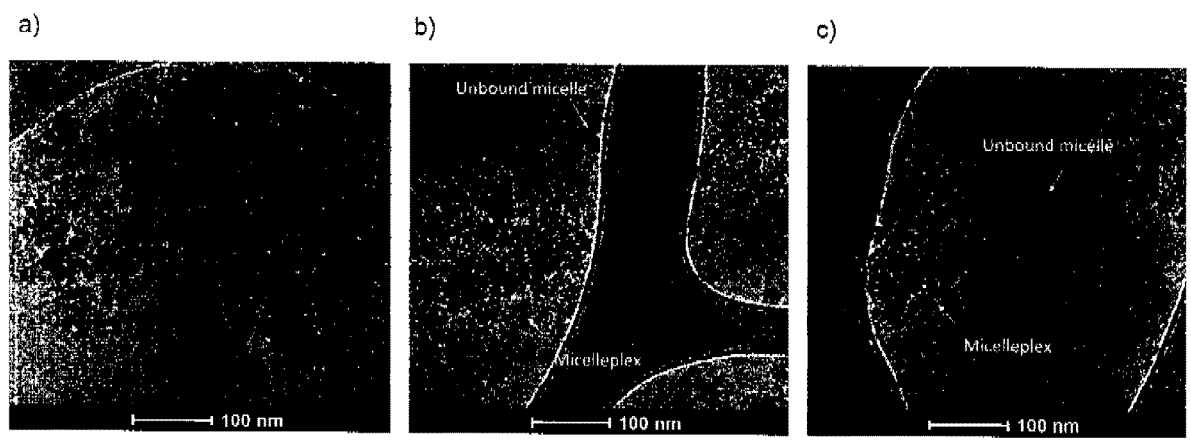
FIGS. 7(a)-(c) are cryo-TEM images in water of (a) RNPs, (b) micelleplexes at ODB(10) polymer:RNP molar formulation ratio 2.5:1, and (c) micelleplexes at ODB(10) polymer:RNP molar formulation ratio 5:1.

The complexation mechanisms and the morphology of micelleplexes were further corroborated by cryogenic transmission electron microscopy (cryo-TEM) as displayed in FIGS. 6(a)-(d) and FIGS. 8(a)-(c). The single micelles and RNPs were able to be clearly imaged prior to complexation in PBS (FIG. 6(a)-7(b)). It is worth noting that while the micelle core is visible, the corona consisting of the solvated PDMAEMA and PEO blocks has a lower electron density and is not visualized due to the low contrast (FIG. 6(a)). After micelleplex formation, the micelle corona has an increased contrast due to RNP binding and becomes visible (FIG. 6(c)-(d)), and discrete RNPs can be visualized as higher contrast spots within the micelle corona. Due to RNP payload loading and increased contrast, the size of RNP-micelle complexes appears visually larger in the cryo-TEM compared to the image of the micelles, even though in the DLS data, the overall hydrodynamic diameter actually contracts to promote complexation. Moreover, the micelleplexes in PBS appear to be spherical, and all micelleplexes contain single micelles, which is also in agreement with the previous DLS data. At ODB(10) polymer:RNP molar formulation ratio 2.5:1, some RNPs can be visualized in an uncomplexed free RNP state (FIG. 6(c)), and the amount of free RNP is largely reduced at higher polymer formulation ratio (ODB(10) polymer:RNP 5:1), which is evident by the lack of free RNP in the cryo-TEM image in FIG. 6(d). In contrast, when the RNPs are diluted in water, they form large multi-protein aggregates of various sizes (FIG. 7(a) and 13). After formulation with the micelles, the micelleplexes clearly exhibit smaller sizes compared to RNP only (FIG. 7(b)-(c)), which is consistent with our previous data and hypothesis that formation of micelleplexes help break up the larger aggregates of RNPs. This could also be the reason why the ODB(10) micelle with the longest PEO block performs better than the other micelle variants. The long PEO corona can potentially provide effective hydrophilic shielding and thus have better stabilization effect to the micelleplexes. In addition, free unbound micelles can also be visualized at both polymer:RNP ratios, which is opposite to the observation in PBS. These images provide further evidence of the different complexation mechanisms of micelleplex formation in PBS and water, which influences their biological performance.

Figure 8:
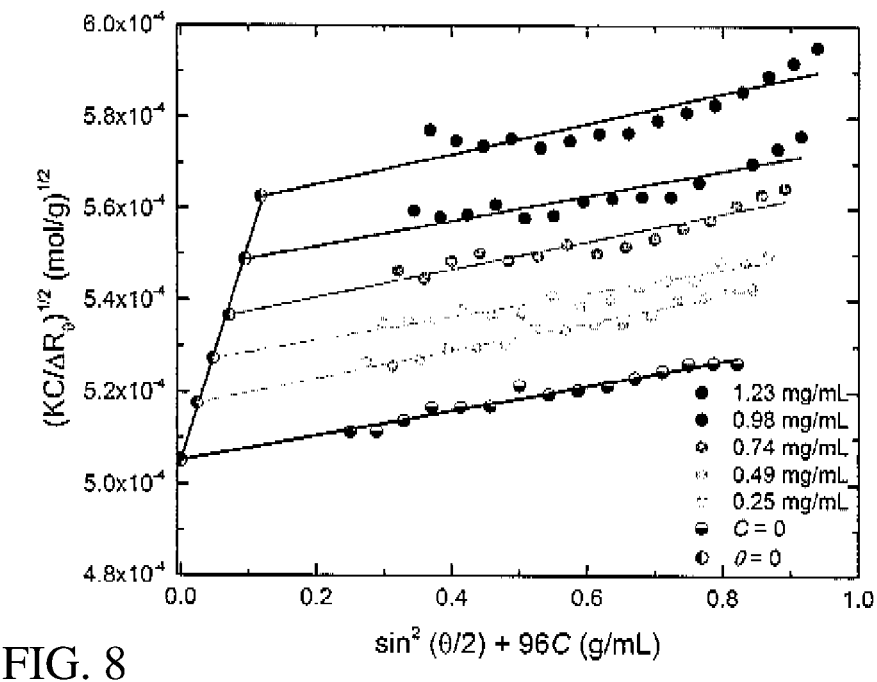
FIG. 8 is a plot of a Berry analysis from static light scattering experiments of micelles in PBS buffer (pH=7.4 and ionic strength=154 mM).
Figure 9:
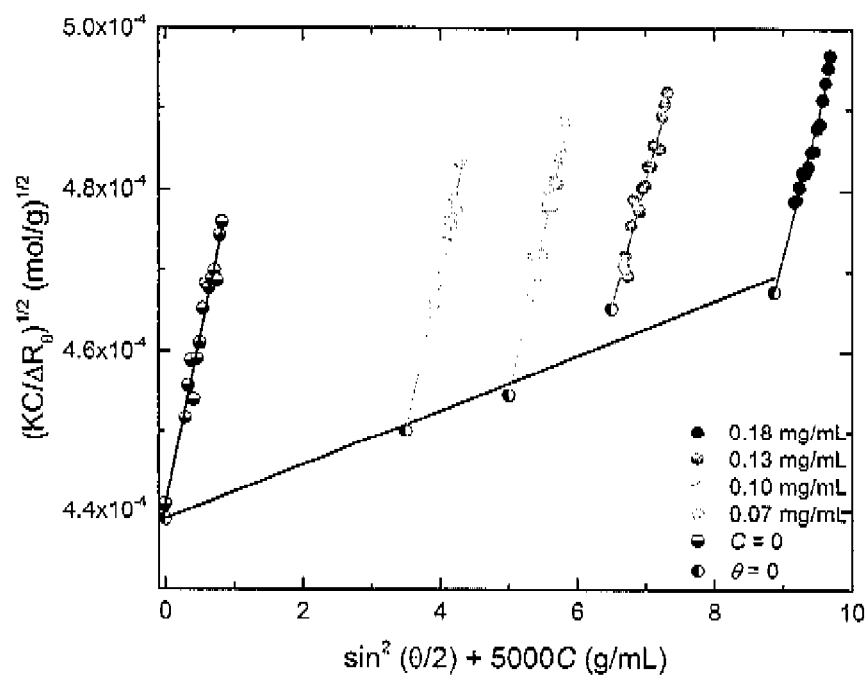
FIG. 9 is a plot of a Berry analysis of micelleplexes (with RNP) at ODB(10) polymer:RNP molar ratio 2.5:1 in PBS buffer (pH=7.4 and ionic strength=154 mM).

Based on the DLS and cryo-TEM results, uniform micelles and micelleplexes are formed in PBS, thus enabling further quantitative analysis via static light scattering (SLS). Berry plots were used to extract the radius of gyration ($R_g$) and weight-averaged molar mass ($M_w$) of micelles and micelleplexes (FIGS. 8-9). The ratio between $R_g$ and $R_h$ can provide conformation and shape information of polymers and complexes. Bare micelles without RNPs exhibited an average $R_g$ of 22 nm, and the $R_h$ of micelles were measured to be 30 nm by DLS (FIG. 5(a) and Table 2).

Thus, the $R_g/R_h$ value of the bare micelles was calculated to be 0.73, close to that of a hard sphere (0.78). The $M_w$ of micelles was measured to be $3.9 \times 10^6$ g/mol. With the assumption that all micelles are uniform and share the same composition, and given that each polymer chain has an $M_w$ of $6.2 \times 10^4$ g/mol, an average of 63 polymer chains per ODB (10) micelle are calculated to be present per micelle (micelle aggregation number $N_{agg}$=63). Thus, when formulated with the RNPs at ODB(10) polymer:RNP molar ratios 2.5:1 and 5:1, the micelle:RNP molar formulation ratios are 1:25 and 1:13, respectively. Micelleplex composition and properties at polymer:RNP molar ratio of 2.5:1 were also characterized by SLS. This result indicated a $R_g$ of 29 nm, bigger than the $R_g$ of micelle only, due to the increased weight and density on micelleplex corona after RNP binding. With the $R_h$ of 26 nm tested by DLS, micelleplexes have a $R_g/R_h$ value of around 1.1, closer to that of a soft sphere (1.0). The $M_w$ of ODB(10)-RNP micelleplexes was calculated to be $5.2 \times 10^6$ g/mol. Under the assumption that every micelleplex contains the same number of RNPs and that all micelles were complexed, we calculate that each micelle housed on average 14 RNPs (calculation detailed in the Supporting Information). Thus, under polymer:RNP ratio 2.5:1, which is micelle:RNP molar ratio 1:25, around 56% of RNPs were bound to the micelles, indicating that some free RNP exists in the solution, which is in agreement with the cryo-TEM images where the free unbound RNPs can clearly be visualized (FIG. 7(c)). In comparison, at a polymer:RNP molar ratio 5:1, which is a micelle:RNP molar ratio of 1:13, the number of micelles is sufficient to house all the RNPs, thus there should be no free RNP in solution, which is also in agreement with the cryo-TEM results (FIG. 6(d)). The quantitative properties of the micelles and micelleplex solutions are summarized in Table 3.

TABLE 3

Quantitative Characterization and Analysis of Micelles and Micelleplexes

| Properties | Micelle | Micelleplex[a] |
|---|---|---|
| $M_w$ (g/mol)[b] | $3.9 \times 10^6$ | $5.2 \times 10^6$ |
| $R_g$ (nm)[b] | 21 | 29 |

TABLE 3-continued

Quantitative Characterization and Analysis of Micelles and Micelleplexes

| Properties | Micelle | Micelleplex[a] |
|---|---|---|
| $R_g/R_h$ | 0.73 | 1.1 |
| $A_2$ (cm$^3$mol/g$^2$)[b] | $2.3 \times 10^{-5}$ | $8 \times 10^{-5}$ |
| $N_{agg}$[c] | 63 | — |
| # amine/micelle[d] | 9,500 | — |
| pKa of PDMAEMA block[25] | 7.8 | — |
| Percent amine protonated at pH = 7.4 | 73% | — |
| # protonated amine/micelle | 7,000 | — |
| RNP/micelle feed ratio | — | 25:1 |
| RNP/micelle binding ratio[e] | — | 14:1 |
| # micelle/complex[f] | — | 1 |
| Percent RNP bound | — | 56% |

Quantification of ODB(10) Micelleplex Gene-Editing Efficiency

Figure 10:
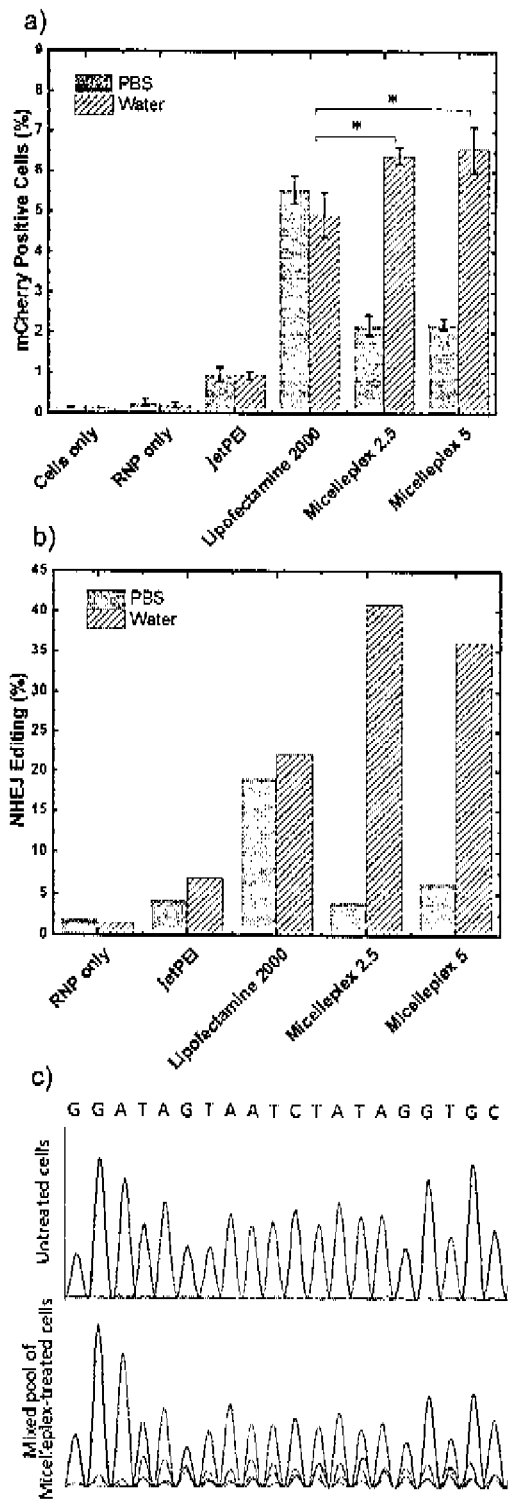
FIGS. 10(a)-(c) are plots of in vitro gene editing achieved by ODB(10) micelleplexes (with RNP) in HEK 293T TLR cells using formulation conditions in PBS and water at polymer:RNP ratios of 2.5:1 and 5:1 along with controls.

HEK 293T TLR cells were transfected with ODB(10) micelleplexes, and 48 hr after transfection, the percent mCherry+ cells were measured quantitatively by flow cytometry. The results revealed that the micelleplexes formed in PBS produced around 2.2% mCherry+ cells for both RNP:micelle molar ratios, which is higher than the 1.0% produced with the jetPEI positive control, but lower than Lipofectamine 2000 (FIG. 10(a)). Micelleplexes formed in water, however, offered 6.4-6.6% mCherry+ cells, which is higher than the 4.9% of mCherry+ cells with Lipofectamine 2000. These data showed a similar trend to the high content screens comparing the performance of ODB(10) micelles to the controls. As discussed previously, only a fraction of the indels generated by gene-editing lead to the correct frame shift to promote expression of mCherry protein; thus, this assay is a significant underestimation of total gene editing in the cellular population.

To further quantify and compare the total gene-editing efficiency of the micelleplex formulations and controls, capillary Sanger sequencing was applied to the targeted genome locus of the HEK 293T TLR cell line for all transfected samples. A TIDE (Tracking of Indels by DEcomposition) computational assay[46] was then utilized to analyze the data. Briefly, the TIDE assay compares the wild-type untreated cell DNA sequence, acquired from standard Sanger sequencing, with the DNA sequence of edited samples, and generates the frequency of targeted mutations. At ODB(10) polymer:RNP molar ratios of 2.5:1 and 5:1, the micelleplexes in PBS showed a total gene editing of 4% and 6.3%, respectively (FIG. 10(b), solid blue bars). Although this gene-editing efficiency is moderate, the small, uniform, and well-defined nature of this micelleplex system yields the potential for further optimization for in vivo gene editing. Interestingly, a significant boost in the gene-editing efficiency was achieved by the micelleplex formulations in water. The data showed that slightly over 40% of the cells undergo NHEJ after treatment by the micelleplexes at polymer:RNP 2.5:1, which is significantly higher than that observed with jetPEI and approximately doubled the efficiency of Lipofectamine2000 (FIG. 01(b), slashed pink bars). The sequencing chromatograms of the DNA extracted from cells treated by micelleplexes clearly showed a mixed pool of edited and wild-type cellular DNA (FIG. 01(c)), which is a further indication of the successful and high efficiency gene editing.

It is intriguing that the micelleplex formation conditions have such a significant impact on micelleplex complexation and gene-editing efficiency. While not wishing to be bound by any theory, we speculate that the larger micelleplex particle size formed in water is the key to higher in vitro transfection efficiency. Indeed, previous studies with pDNA delivery have shown that solvent ionic strength significantly impacts vehicle-pDNA complex formation, size, and colloidal stability. The previous reports also mentioned that large particle size may play a significant role in accelerating sedimentation of the complexes in cell culture, which promotes a higher concentration of the complexes to interact with the adherent cell monolayer, and subsequently increase cellular internalization to promote higher transgene expression. However, this is the first time that this phenomenon has been observed in a RNP delivery system. Quantitative treatment of this theory can be provided by the equation for particle sedimentation velocity (Eqn. 1A below).

$$v = \frac{2r^2 g(\rho_p - \rho_f)}{\mu_f}$$

In Equation 1A, $\rho_p$ is the density of particle, $\rho_f$ and $\mu_f$ are fluid density and viscosity, respectively, and g is the gravitational acceleration. With the assumption that micelleplexes formed in water and PBS have similar densities, and the fact that the fluid density and viscosity are the same (as both transfections were completed in culture), the micelleplex sedimentation velocity (v) is then solely proportional to $r^2$, the particle radius. Micelleplexes formed in water have around 5 times larger radii compared to micelleplexes formed in PBS and thus, the sedimentation rate would calculate to be about 25 times faster, which causes a faster accumulation of micelleplexes on the cell surface, presumably increasing cellular uptake, and subsequently leading to significantly higher RNP delivery and gene-editing.

This shows quantitative correlation between formulation conditions and the resultant biological performance, and directly correlates the physico-chemical properties of vehicle-RNP complexes and their genome-editing efficiency. Although large micelleplexes formed in water may be inefficient for in vivo systemic delivery, they could find utility for direct tissue injection. Moreover, their high efficiency could be important and useful for ex vivo or cell therapy-based treatments.

CONCLUSION

Four cationic block polymer micelle systems comprised of diblock PDMAEMA-b-PnBMA and three PEO-b-PDMAEMA-b-PnBMA triblock variants were prepared and studied as CRISPR/Cas9 ribonucleoprotein delivery vehicles. A high-throughput DLS and high content image cytometry workflow was developed to analyze formulations for hydrodynamic size and gene editing efficiency. This workflow enabled the discovery that ODB(10) revealed statistically higher editing efficiency than the Lipofectamine 2000 positive control. For this reason, the ODB(10) micelleplex system was selected for further quantitative characterization. Well-defined micelleplexes were formed with small and uniform particle sizes in PBS buffer and RNPs were shown to bind within the coronas of single micelles, which promoted moderate gene-editing efficiency. Due to the well-defined composition and uniform size, this formulation has potential to be optimized for in vivo gene editing. In comparison, micelleplexes self-assembled in water formed larger multi-micelle particles. While not wishing to be bound by any theory, it is postulated that the micelles complexed to pre-aggregated RNPs enable faster sedimentation kinetics and thus lead to superior gene-editing efficiency in vitro, twice that of Lipofectamine 2000. This facile packaging method to promote high editing efficacy has the potential to be applied for in vitro and ex vivo gene editing. A well-defined polycationic micelle formulation thus successfully complexes and delivers CRISPR/Cas9 RNPs, and enabled correlations of the physico-chemical properties, mechanism of packaging, and efficacy of genome editing. Indeed, the novel results presented herein provide future guidance for utilizing cationic polymer micelles and essential characterization techniques to facilitate simple, efficient, and inexpensive gene editing systems for a wide variety of applications.

Example 2—Delivery of pDNA

Materials and Methods

Materials. All chemicals were purchased from Sigma-Aldrich and used as received: 2-(dimethylamino)ethyl methacrylate (DMAEMA), 4-cyano-4-[(dodecylsulfanylthiocarbonyl) sulfanyl] pentanoic acid (CPDT) as the chain-transfer agent (CTA), 4,4'-azobis(4-cyanovaleric acid) (V-501), and 3-(N-morpholino) propanesulfonic acid (MOPS). Monomers DMAEMA and nBMA were passed through activated neutral alumina to remove inhibitors immediately before use. Phosphate-buffered saline of pH 7.4 (PBS) and Pierce™ Protein Concentrator PES (10 k MWCO, 2-6 mL) disposable ultrafiltration centrifugal devices were purchased from ThermoFisher and used as received. Dialysis tubing (cutoff $M_w$=6-8 kDa) was purchased from Spectra/Por, treated with 0.1 wt % ethylenediaminetetraacetic acid (EDTA) solution, stored in ~0.05 wt % sodium azide solution and triple rinsed with MilliQ water before use. Plasmid DNA (pDNA) pZs-Green (4708 base pairs, encoding green fluorescent protein; GFP) was purchased from Aldevron (1 mg/mL solution in water with <1.00% residual protein). Before use, pDNA was lyophilized and redissolved in PBS buffer. The concentration of DNA solution was measured by UV-Vis spectroscopy, given that the DNA has an extinction coefficient of 0.021 (μg/mL)-1 cm-1 at 260 nm. Cell culture media and reagents, including Dulbecco's Modified Eagle Medium (DMEM, high glucose, GlutaMAX™ supplement), Reduced-Serum Medium (Opti-MEM®, GlutaMAX™ supplement), Trypsin-EDTA (0.25%) and Antibiotic-Antimycotic (100×) were purchased from ThermoFisher. Heat Inactivated Fetal Bovine Serum (HI FBS) was purchased from Atlanta Biologicals (Flowery Branch, Ga.). HeLa cells were purchased from ATCC (CCL-2; Manassas, Va.). The HEK 293T cell line was acquired as a gift from the Mark Osbom laboratory at the University of Minnesota. Cell Counting Kit-8 (CCK-8) was purchased from Sigma-Aldrich (St. Louis, Mo.). JetPEI was purchased from Polyplus-transfection SA (Illkirch, France). CellScrub Buffer was purchased from Genlantis, Inc. (San Diego, Calif.).

Figure 11:
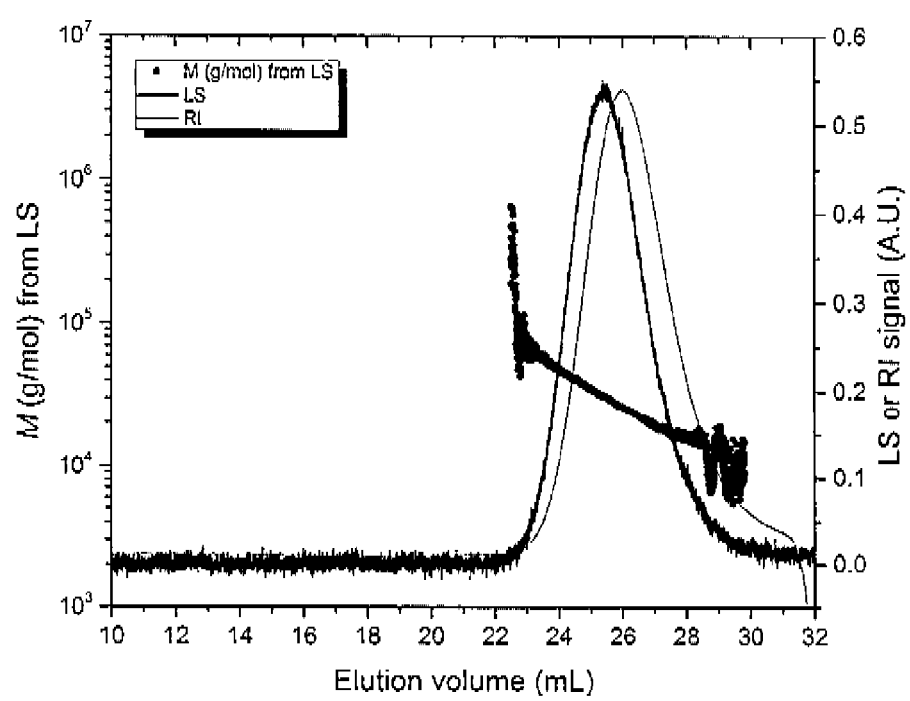
FIG. 11 is plot of molecular weight and dispersity of poly(2-(dimethylamino)ethyl methacrylate) (D) measured by size exclusion chromatography (SEC) with light scattering (LS) and refractive index (RI) detectors.
Figure 12:
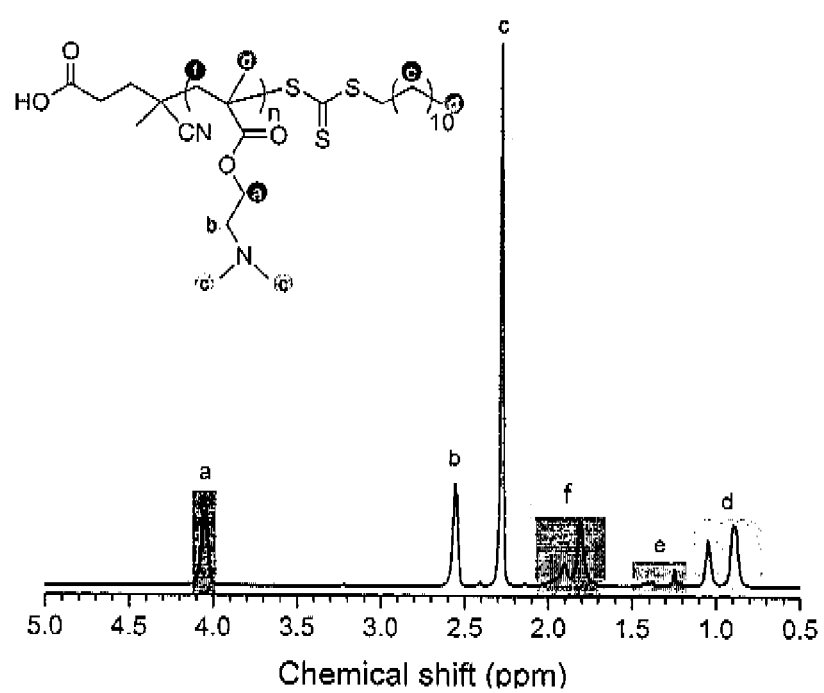
FIG. 12 is the $^1$H NMR spectrum of poly(2-(dimethylamino)ethyl methacrylate) (D) in d-chloroform.

Polymer Synthesis. Homopolymer poly(2-(dimethylamino) ethyl methacrylate) (PDMAEMA, "D"; 25 kDa) was synthesized by RAFT polymerization. Briefly, DMAEMA, CPDT, and V-501 were dissolved in DMF at a 4000:13:1 ratio with final monomer concentration ~30 wt %. The solution was degassed via three freeze-pump-thaw cycles, pressurized with argon, and polymerized at 80° C. for 4.75 h. The polymerization reaction was stopped by cooling the solution in an ice bath. The obtained polymer was purified by precipitation in cold hexane three times, dissolved in benzene, and freeze-dried. The final polymer was a light-yellow powder, and was characterized by SEC-LS, as shown in FIG. 11, and by 1H NMR spectroscopy, as shown in FIG. 12. Block copolymer PDMAEMA-block-poly(n-butyl methacrylate) (27-14 kDa) ("DB") was previously synthesized and characterized according to Sprouse et al. Block polymers poly(ethylene glycol)-block-PDMAEMA (10-28 kDa; "OD") and poly(ethylene glycol)-block-PDMAEM-block-poly(n-butyl methacrylate) (10-28-24 kDa; "ODB") were previously synthesized and characterized according to Jiang et al.

Micelle Formation. DB polymers formed spherical micelles by direct dissolution in deionized water at 1 mg/mL, as described previously by Sprouse et al. 36 ODB micelles were formed by a co-solvent method, as previously described by Jiang et al. Briefly, ODB polymers were dissolved in DMF at 1 wt %. An equal volume of MOPS buffer (pH 7, 100 mM ionic strength) was added drop-wise to the polymer solution while stirring. The micelle solutions were then stirred overnight before dialysis. Both DB and ODB micelles were dialyzed against PBS buffer before use.

Complex Formation. Polyplexes and micelleplexes were formed by direct mixing equal volumes of DNA and polymer solutions. The final DNA concentration was kept constant at 0.031 mg/mL (0.1 mM phosphate group), and the concentration of polycations was varied to achieve the target N/P ratios after mixing. For polyplexes, polycation (jetPEI, D polymer, or OD polymer) solution was added to the DNA solution. For micelleplexes, DNA solution was added to the polycation solution (DB micelles or ODB micelles). This is more comparable with micelleplex formation by titration, where the minor polyelectrolyte is added into the solution of majority polyelectrolyte.

Dynamic Light Scattering. DLS was conducted using a Brookhaven Instrument BI-200DM multi-angle light-scattering instrument with a 637 nm laser. All measurements were performed at 23° C. To minimize the contribution of dust, all vials were triple rinsed with Milli-Q water and acetone before use. All polymer solutions were filtered through 0.2 μm filters and all DNA solutions were filtered through 0.45 μm filters. To avoid potential impact on complex structures due to filtration, complexing solutions were filtered before complexation only. The complex formation process is the same as previously described but using pre-cleaned vials and pipette tips. For each DLS measurement, autocorrelation functions were collected at five angles (30°-120°) for 10 min each. The size distributions were assessed by applying the REPES algorithm to the correlation functions collected at 90°. For samples with monomodal size distributions, a second cumulant model was used to fit the correlation functions. In this case, an average hydrodynamic radius $R_h$ and its dispersity were obtained. For samples with bimodal size distributions, a double exponential decay model was used to fit the correlation functions. In this case, average hydrodynamic radii for two populations were obtained.

Cell Culture HeLa and HEK 293T cells were cultured in 75 $cm_2$ cell culture flasks with Dulbecco's Modified Eagle Medium (DMEM) containing 10% HI FBS and 1% antibiotic and antimycotic solution as culture media. The temperature of the incubator was kept at 37° C. under a humidified atmosphere with 5% $CO_2$. Cell confluency was monitored, and cells were passaged as needed.

GFP Expression Assay Cells were seeded in 24-well plates 24 h before transfection at 50,000 cells/well density in 1 mL DMEM/well containing 10% HI FBS. JetPEI samples were prepared and transfected following the manufacturer's protocol (N/P=5). Polyplexes and micelleplexes were prepared 1 h before transfection. Polyplexes were formed by adding 60 µL pDNA solution (60 ng/L) to the same volume of polymer solution at appropriate concentrations to achieve N/P=5 and 10. Micelleplexes were formed by adding 60 µL micelle solution at an appropriate concentration to the same volume of pDNA solution (60 ng/L) to achieve N/P=5 and 10. The polyplex and micelleplex formation conditions were kept consistent with all the other experiments in this work. Immediately before transfection, 120 µL of complex solutions were diluted with 240 µL PBS solutions, and then mixed with 720 µL of Opti-MEM. In each well, DMEM cell culture media was aspirated, and then 300 L complex solution was added (n=3). At 4 h after transfection, 1 mL DMEM containing 10% HI FBS was added. Cell culture media was replaced with fresh DMEM containing 10% FBS 24 h after transfection. At 48 h after transfection, cell culture media was removed, and cells were lifted by adding 0.5 mL trypsin. Cells from each well were suspended in 1 mL of ice cold fresh DMEM with 10% FBS, centrifuged, and resuspended in DMEM with 4% propidium iodide (dead cell stain). GFP expression was analyzed by flow cytometry using a FACSVerse instrument (San Jose, Calif.) with a 488 nm 40 mW solid state laser to excite GFP. Data were analyzed with FlowJo (V10) software.

Cytotoxicity Hela and HEK 293T cells were cultured and transfected following a similar procedure as in the GFP expression assay but in 48-well plates (n=4). Cell culture media was replaced by DMEM containing 10% FBS and 20 µL CCK-8 solution to each well, 48 h after transfection. Cells were then incubated under 37° C. for 4 h. Light absorbance was measured with a Biotek Synergy H1 plate reader at 450 nm. Untreated cells were normalized to 100% cell survival, and cell viability was calculated from the ratio of the light absorbance of transfected cells to untreated cells.

Cellular Internalization HeLa cells were prepared and transfected as described in the GFP Expression Assay section. The plasmid used in this assay was labeled with Cy5 DNA labeling kit (Mirus, Madison, Wis.) and purified through ethanol precipitation. Polyplexes and micelleplexes were removed from wells 4 h after transfection, cells were washed with PBS, and treated by 0.5 mL CellScrub buffer for 10 min to remove any residual polyplexes or micelleplexes attached to the cell surface. Then, cells were washed twice with PBS to remove residual CellScrub buffer. Fresh DMEM containing 10% FBS was then added to each well, and the well plate was put back to the incubator and cells were incubated at 37° C. with 5% $CO_2$ overnight. Twenty-four hours after transfection, cells were prepared for flow cytometry as described above in the GFP Expression Assay section. Percent $Cy5_+$ cells and percent $GFP_+$ cells were counted using a FACSVerse instrument with a HeNe laser to excite Cy5 (633 nm) and a 488 nm 40 mW solid-state laser to excite GFP. Data were analyzed by FlowJo (V10) software.

Pulsed-Field-GradientNMR For the PFG-NMR experiments, PBS buffer was prepared with $D_2O$ and phosphate buffered saline 10× powder at pD=7.4 (Fisher BioReagents, Fisher Scientific). OD polymer and lyophilized pDNA were directly dissolved in deuterated PBS buffer. For ODB micelles, solvent exchange to deuterated PBS buffer was achieved with filtration centrifugal devices, in which micelles were repeatedly concentrated and rediluted by deuterated PBS. After solvent exchange, the micelle concentration was calculated using the final volume of the micelle solution, assuming no mass loss during the solvent exchange process. OD polyplexes and ODB micelleplexes were prepared following the same procedure with polycation and pDNA solutions in deuterated PBS buffer.

Figure 13:
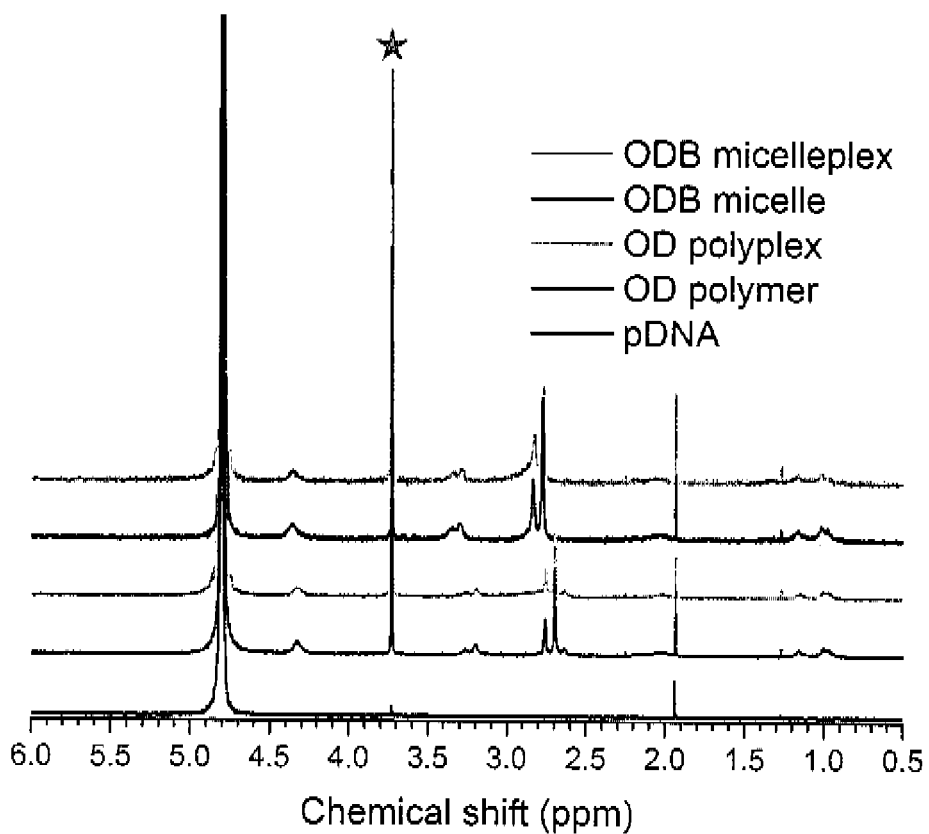
FIG. 13 is the $^1$H NMR spectrum of pDNA, poly(ethylene glycol)-block-poly(2-(dimethylamino) ethyl methacrylate) (OD), OD polyplex, ODB micelle, ODB micelleplex solutions in PBS buffer salts with $D_2O$ at 23° C. Polyplexes and micelleplexes were prepared at N/P=5. The concentrations of pDNA and polymers are the same as in the PFG-NMR experiments. The highlighted peak (with the star) is the proton signal from the PEG block that was used to measure translational diffusion coefficient of polymers and complexes.

PFG-NMR experiments were performed on a Bruker Avance III500 MHz NMR instrument at 23° C. In a typical experiment, a simulated pulse sequence (longitudinal eddy current delay experiment using bipolar gradients acquired in 2D, namely "ledbpgp2s") was applied and a series of 1D $^1H$ spectra were obtained and analyzed by Topspin 3.5 software. The proton from the PEG block (3.727 ppm in PBS buffered $D_2O$) produced the most well-defined peak, as shown in FIG. 13, and therefore was used for analysis. The observed intensity (I) of this peak was measured at each input gradient strength G (from 2 to 95%) to extract the translational diffusion coefficient $D_t$. For a monomodal system, such as OD polymer, $D_t$ was obtained using the Equation 1B below, where $I_o$ is the intensity at G=0, γ is the gyromagnetic ratio of $_1H$ (42.6 MHz/T), δ is the length of the gradient pulse (5 ms) and Δ is the diffusion time. Experimentally, Δ were set to 500 ms for OD polymers and polyplexes, and to 600 ms for ODB micelles and micelleplexes:

$$\ln\left(\frac{I}{I_o}\right) = -\gamma^2 G^2 \delta^2 D_t\left(\Delta - \frac{\delta}{3}\right)$$

Using Equation 1B, the value of t was obtained as the slope of the linear fit to $\ln(I/I_o)$ plotted against $-\gamma_2 G_2 \delta_2(\Delta-\delta/3)$. For a bimodal system, such as OD polyplexes, the fraction of bound polycation $f_{bound}$ can be estimated using Equation 2B:

$$\frac{I}{I_o} = f_{bound}\exp\left(-\gamma^2 G^2 \delta^2 D_{t,c}\left(\Delta - \frac{\delta}{3}\right)\right) + \\ (1-f_{bound})\exp\left(-\gamma^2 G^2 \delta^2 D_{t,f}\left(\Delta - \frac{\delta}{3}\right)\right)$$

In Equation 2B, $f_{bound}$ is the fraction of bound OD polymers in the complexes with the diffusion coefficient of $D_{t,c}$, and the free OD polymers has a diffusion coefficient of $D_{t,f}$. This equation is valid when the molecular exchange rate between the free polycations and the bound polycations is very low on the time scale of the diffusion experiments.

Static Light Scattering (SLS) For SLS measurements, a Brookhaven Instrument BI-200DM multi-angle light-scattering instrument with a 637 nm laser was used, and toluene was used for calibration ($R_\theta$=1.363×10$^{-5}$ cm$^1$). ODB micelleplexes were formed at the same concentration as described previously in DLS section, and then diluted to lower concentrations for the construction of a Berry plot.

Cryogenic Transmission Electron Microscopy (cryo-TEM). Vitrified samples for cryo-TEM were prepared using a FEI Vitrobot. For each sample, ~4 µL of solution was transferred to a lacy carbon/Formvar grid in the climate-controlled chamber of the Vitrobot, which was maintained at 26° C. and maximal humidity. The grid was treated using a PELCO easiGlow glow discharge cleaning system immediately before use. In the chamber, the loaded grid was then blotted for 5 s, rested for 1 s, and plugged into liquid ethane surrounded by liquid nitrogen. The vitrified samples were subsequently transferred into and stored in liquid nitrogen before imaging. Vitrified samples were imaged using a FEI Tecnai G2 Spirit BioTWIN microscope coupled with a single-tilt cryo holder and a CCD camera (2048×2048 pixels). The scope was operated at 120 kV and images were captured at under focus for adequate contrast.

Circular Dichroism (CD). Circular dichroism spectra were obtained using JASCO J-815 Spectropolarimeter. The solutions were loaded into a Sterna 1 mm path quartz cuvettes and the CD spectra were collected over the range 200-340 nm at 50 nm/min rate for three iterations. The complexes were formed on the day of the measurements.

System Design

Figure 15:
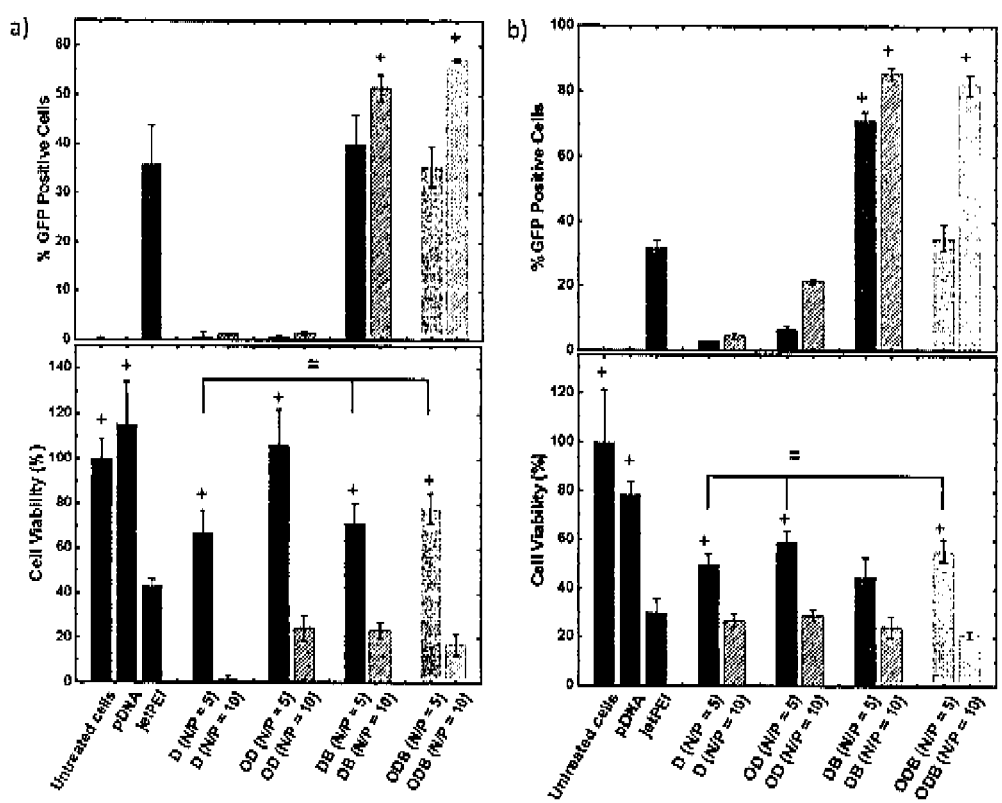
FIG. 15 are plots for micelleplexes' pDNA delivery efficiency and toxicity.

A series of polymers containing the same cationic block (each chain carrying approximately 170 amine groups) with distinct chemical compositions and assembly properties, as shown in FIG. 2, were prepared via reversible addition-fragmentation chain transfer (RAFT) polymerization. The hydrophilic polymers D and OD were mostly molecularly dissolved in phosphate buffered saline (PBS). As Table 5 and FIG. 15(a) show, a small fraction of polymer D was found to aggregate, presumably due to the presence of the dodecyl chain end from the chain transfer agent 4-cyano-4-[(dodecylsulfanylthiocarbonyl)sulfanyl]pentanoic acid. The DB and ODB variants were designed with similar respective D and OD block lengths, but with an additional hydrophobic poly(n-butyl methacrylate) block. These two amphiphilic variants self-assembled into well-defined spherical micelles of core-shell and core-shell-corona structures, respectively.

As shown in Table 5, DB and ODB micelles have similar hydrodynamic radii (Rh of about 30 nm) in PBS at pH 7.4 and similar core radii (Rc~10 nm). The core of these micelles is kinetically constrained from chain exchange at room temperature.34,35 The micelle coronas, on the other hand, are responsive to changes in solution environment36 and are concentrated with amine groups (>104 amine groups/micelle). The pDNA used in this study encodes green fluorescence protein (GFP) and has 4708 base pairs per chain (9416 phosphate groups/chain) with a Rh of 75 nm in PBS buffer.

TABLE 5

Polymer and Micelle Properties

| Short name | D | OD | DB | ODB |
|---|---|---|---|---|
| $M_n$ (kDa)$^a$ | 25 | 42 | 38$^b$ | 74 |
| $M_{n,\,O}$ (kDa) | — | 10 | — | 10 |
| $M_{n,\,D}$ (kDa)$^c$ | 25 | 28 | 27$^a$ | 28 |
| $M_{n,\,B}$ (kDa)$^c$ | — | — | 14 | 24 |
| Đ$^a$ | 1.13 | 1.12 | 1.10$^b$ | 1.14 |
| $R_h$ (nm) in PBS buffer$^d$ | 3.1 & 46 | 4.6 | 28 | 34 |
| Dispersity$^d$ | | 0.38 | 0.04 | 0.001 |
| $R_c$ (nm)$^e$ | — | — | 8 | 11 |
| # of amine groups/chain or micelle$^f$ | 160 | 180 | $1.6 \times 10^4$ | $2.5 \times 10^4$ |

DB polymer and micelle were previously characterized by Sprouse et al.[36]
OD and ODB polymer and micelles were previously characterized by Jiang et al.[23]
$^a$Determined by SEC-LS;
$^b$determined by MALDI-TOF-MS;
$^c$Determined by $^1$H NMR spectroscopy from the O block, except for DB determined from the ratio of DMAEMA/nBMA;
$^d$Determined by DLS, dispersity taken as $\mu_2/\Gamma^2$ at 90° for monomodal samples;
$^e$Calculated using the $M_w$ determined by SLS of the micelles, assuming the micelle core is free of solvent and has the same density as PnBMA (1.07 g/cm$^3$).

Complex Formation.

Figure 14:
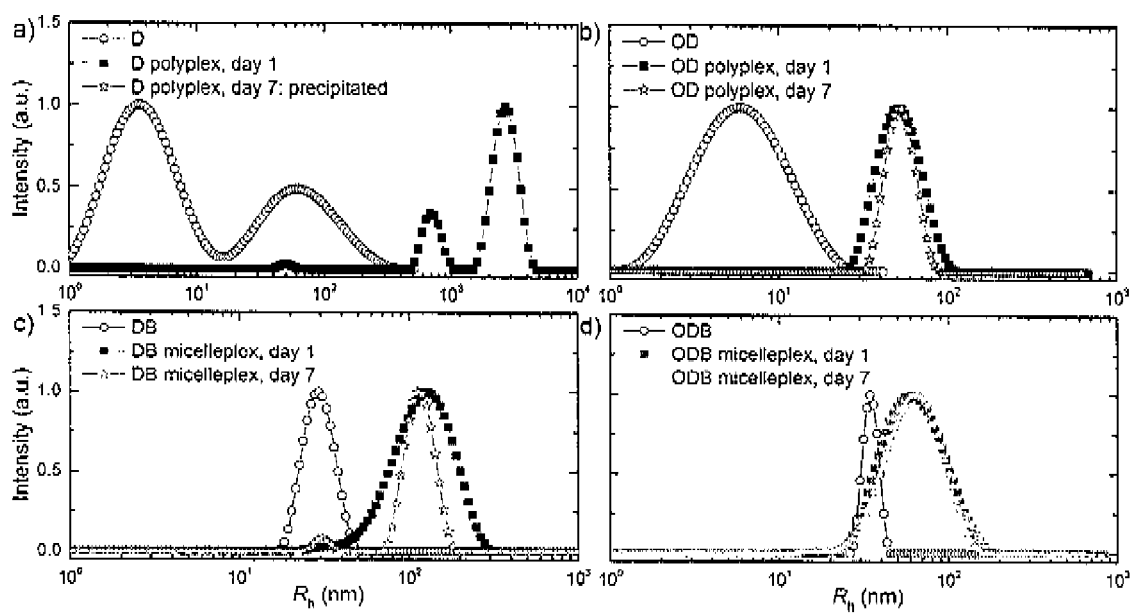
Figure 14:
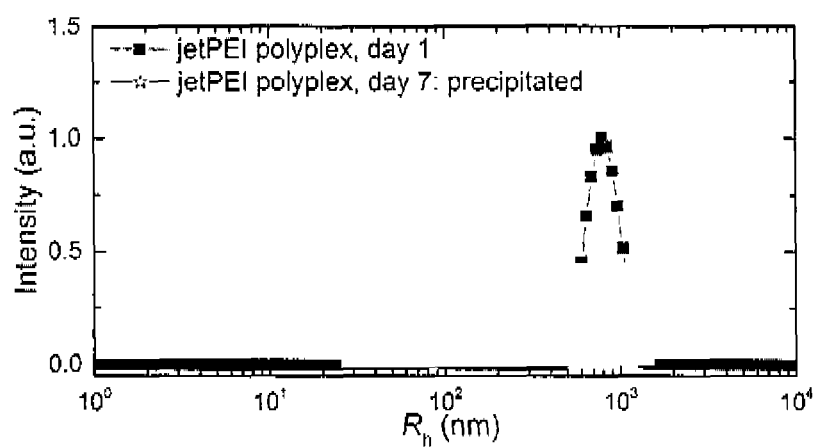
Figure 14:
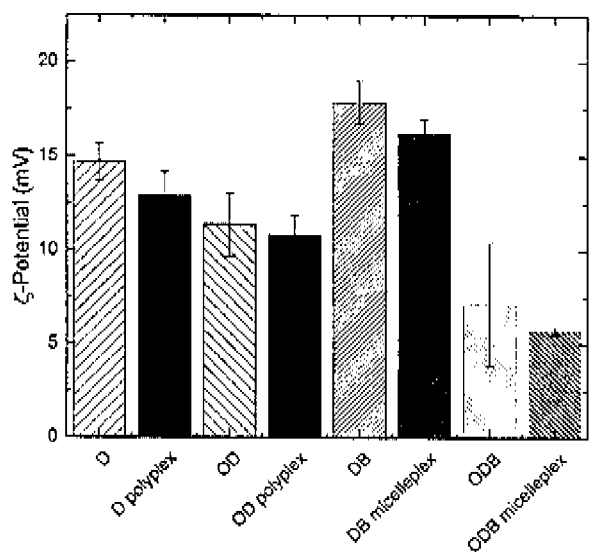

The size, charge, and colloidal stability of polyplexes and micelleplexes were characterized by a combination of dynamic light scattering (DLS) and ζ-potential measurements, which revealed that pDNA chains are packaged very differently between polyplexes and micelleplexes. In PBS, complexes were formed by direct mixing of equal volumes of pDNA and polymer solutions. The ratio of polymer to pDNA is reported as N/P, defined as the total number of amine groups from polycations to the total number of phosphate groups from DNA. At N/P=5, polyplexes formed with D (D polyplexes) were large aggregates at day 1 with $R_h$>400 nm, as shown in FIG. 14(a), and which precipitated within one week after formulation. This result is similar to that seen with polyplexes formed with the commercial polymeric transfection agent jetPEI, as shown in FIG. 14(e), and is as expected, since polyplexes formed with cationic homopolymers that lack a nonionic corona block often suffer from poor colloidal stability. Interestingly, the DB micelleplexes were much smaller ($R_h \approx 100$ nm) and stable in solution over one week, as shown in FIG. 4(c). With the addition of a hydrophilic PEG block, OD polyplexes formed were small ($R_h \approx 50$ nm), uniform, and colloidally stable. Interestingly, ODB micelleplexes also have a similar mean $R_h \approx 53$ nm. The ζ-potential of the micelles were similar to the complexing polycations, as shown in FIG. 14(f). Among all complexes, DB micelleplexes have the highest ζ-potential (16±1 mV) due to the highly concentrated and exposed amine groups in the micelle corona, and ODB micelleplexes have the lowest (6±0.2 mV), due to the effective shielding of the outer PEG corona. Although all four polycations contain the same cationic block, their different architectures contribute to the diverging motifs and colloidal stabilities of their complexes with pDNA. Consequently, they behave quite differently as gene delivery vehicles, vide infra.

Delivery Efficiency The ability of the polyplexes and micelleplexes to deliver pDNA was evaluated and compared by delivering a green fluorescence protein (GFP)-encoding gene (pZsGreen-N1). Polyplexes were removed from cell culture media and percent GFP-positive (GFP$_+$) cells were counted 48 h after transfection. The results revealed that micelleplexes achieved superior gene expression efficiency compared to their corresponding polyplexes, while maintaining a similar level of cytotoxicity. As shown in FIG. 15(a), D and OD polyplexes exhibited less than 1% GFP$_+$ cells at N/P=5 with HeLa cells, whereas DB and ODB micelleplexes produced more than 30% GFP$_+$ cells. By increasing the N/P ratio to 10, the transgene expression increased significantly. At N/P=10, both DB and ODB micelleplexes produced >45% GFP$_+$ cells, higher than the jetPEI positive control. In contrast, the transfection efficiency of D and OD polyplexes remained below 2%. Although the architecture of the polycation significantly impacts the transfection efficiency of the resulting complexes, the cytotoxicity (measured by cell viability) was similar among all four complex types with HeLa cells. At N/P=5, cells treated with all four variants exhibited higher viability compared to jetPEI. With a further increase in the N/P ratio, the cell viability decreases, which is commonly observed for polymeric delivery vehicles.$_{9,37}$ Gene expression and cytotoxicity trends with HEK 293T cells were found to be similar to those observed with HeLa cells (FIG. 15(b)). At N/P=5, D and OD polyplexes show less than 10% GFP$_+$ cells, whereas DB micelleplexes produced greater than 70% GFP$_+$ cells. At a higher N/P ratio of 10, >80% of HEK 293T cells were GFP$_+$, which is more than double that observed for jetPEI.

The observation that the architecture of polycation assembly can dramatically affect the transfection efficiency of pDNA payloads (despite the cationic block having the same identity and length) is intriguing. To understand the underlying mechanism, several additional physical and biological properties were characterized and compared: 1) cellular internalization efficiency and mechanism, 2) amine density of the complexes and their interactions with a lipid membrane, and 3) complex structure, stability, and integrity that influence pDNA accessibility and release once within the cells. While not wishing to be bound by any theory, we hypothesized that by pre-assembling polycations into micelles, one or more of the above aspects are altered, leading to the enhanced gene transfection efficiency of micelleplexes compared to polyplexes.

Cellular Internalization As the first barrier to cellular gene delivery, internalization is often closely related to transfection efficiency. Different complex structures could lead to disparities in uptake efficiencies and pathways. Cy5-labeled pZsGreen plasmid was used to study the internalization efficiency of the complexes. In this experiment, complexes were co-incubated with cells for 4 h and then removed. Cells were then treated with CellScrub solution to completely remove complexes attached to the cell surface. The percentages of Cy5-positive ($Cy5_+$) and $GFP_+$ cells were quantified by flow cytometry 24 h after transfection to understand the relationships among physical properties, cell entry, and gene expression. It should be noted that the percentage of $GFP_+$ cells observed here is lower compared to the GFP expression assay displayed in FIG. 16(a) due to the shorter polyplex/micelleplex contact time with the cells (4 h instead of 24 h) and shorter time for trafficking and gene expression (24 h instead of 48 h). As detailed in FIG. 16(a), fewer than 60% of cells treated with D and OD polyplexes were $Cy5_+$. In comparison, more than 90% of cells in samples treated with DB and ODB micelleplexes were $Cy5_+$. This indicates that micelleplexes enter cells more effectively than polyplexes. The percentage of cells expressing protein ($GFP_+$) among those that internalized complexes ($Cy5_+$) were analyzed. FIG. 16(b) reveals that for cells treated with D and OD polyplexes, only 1-2% of $Cy5_+$ cells also show GFP signals. Thus, although around 35-60% of the cells internalized polyplexes, only a very small fraction of those cells had polyplexes successfully delivered to the nucleus. In comparison, around 10-20% of the cells that internalized micelleplexes also expressed GFP protein at the 24 h time point (FIG. 16(b)), which is much higher than polyplexes. The flow cytometry scatter plots in FIG. 16(c) further reinforce this observation in a qualitative manner, with Q2 denoting cells that are both $Cy5_+$ and $GFP_+$. It is clear that the Cy5/GFP double positive population for cells treated by micelleplexes is much greater than the cells treated by polyplexes.

To understand how the mechanism of endocytosis might be impacted by complex composition and architecture, a pharmacological inhibition study of the different internalization routes was undertaken. Amantadine, Filipin III, and 5-(N,N-dimethyl)amiloride hydrochloride (DMA) endocytosis pathway inhibitors were introduced to cell culture media during transfection to inhibit clathrin, caveolae, and micropinocytosis endocytosis pathways, respectively. Interestingly, the internalization of both polyplexes and micelleplexes were predominantly inhibited by Filipin III, a drug that inhibits caveolae-mediated endocytosis (FIG. 17). As a result, both polyplexes and micelleplexes appear to be internalized primarily through the same caveolae-mediated endocytosis pathway. Thus, the internalization mechanism is likely not the cause of the biological differences observed between polyplexes and micelleplexes. The higher gene expression level for micelleplexes once they have entered the cell could possibly be due to higher endosomal escape efficiency caused by a higher amine density per complex. Moreover, the differences in complexation structure could lead to distinctive pDNA accessibility/release once inside the cells, as further evaluated and discussed below.

Figure 18:
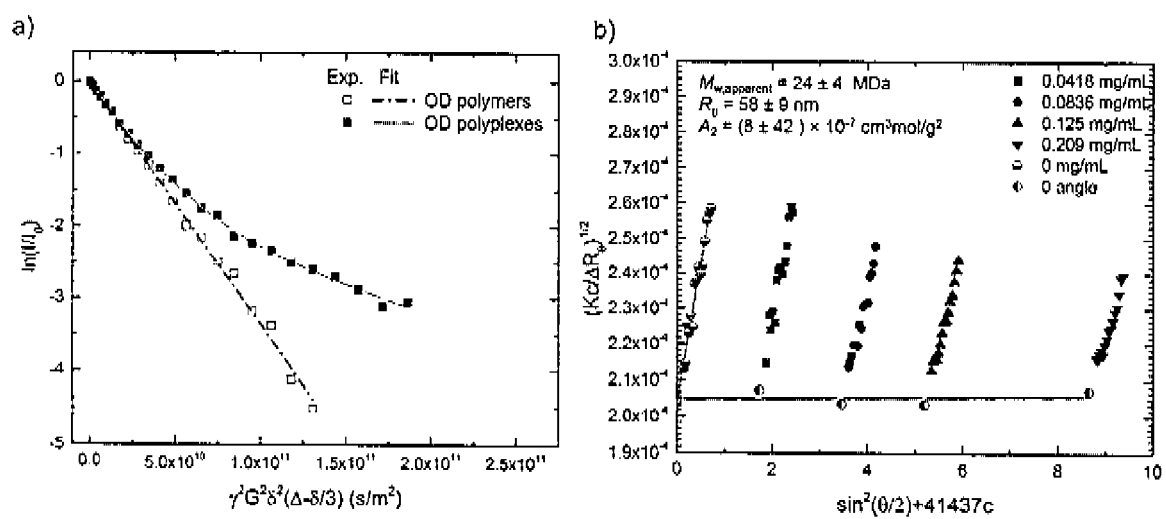
FIGS. 18(a)-(b) are plots of polyplex and micelleplex (with pDNA) composition analysis.
Figure 19:
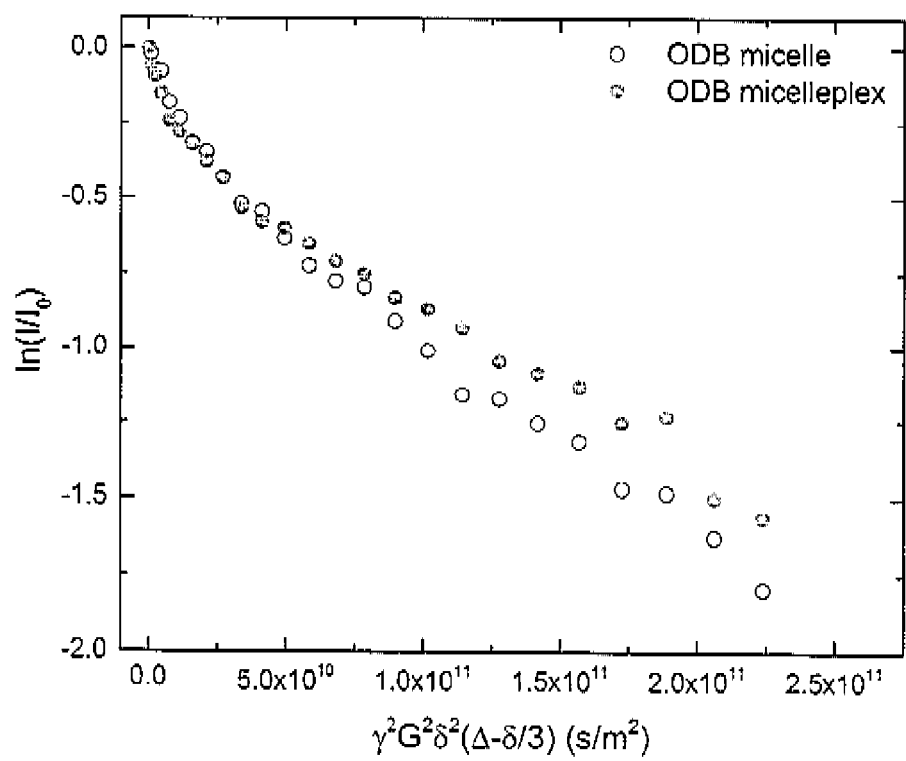
FIG. 19 is a plot of echo decay curves of the protons from the O block in the ODB micelle and ODB micelleplex (with pDNA) at N/P=5 in PBS buffer with $D_2O$ at 23° C. The $\Delta$=600 ms and $\delta$=5 ms.
Figure 20:
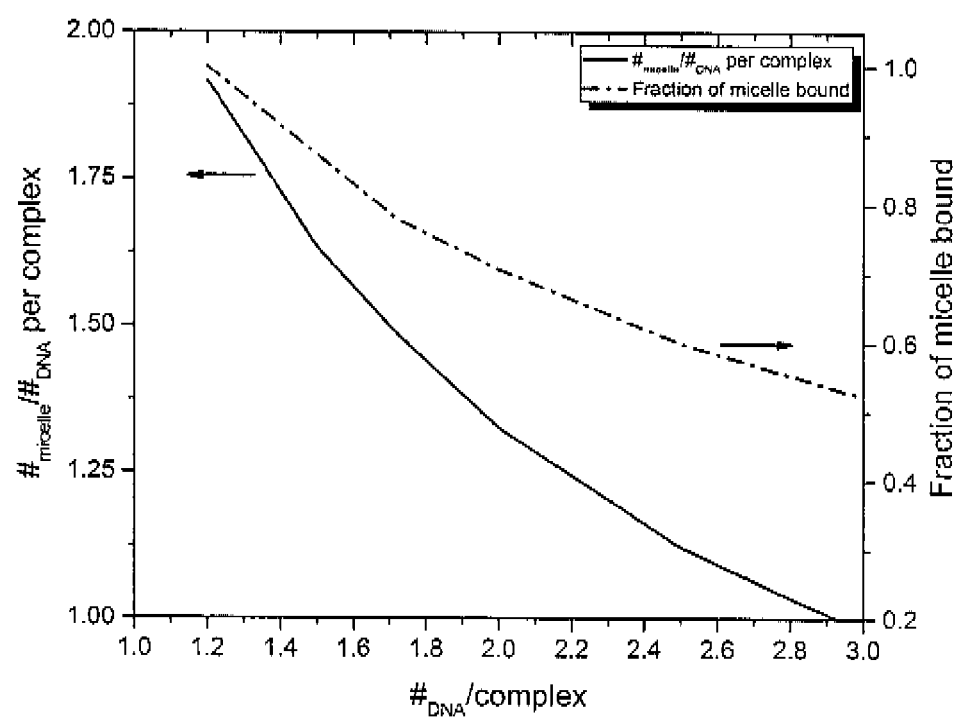
FIG. 20 is a plot of the composition analysis of ODB micelleplexes (with pDNA) in PBS buffers at N/P=5.

Complex Composition and Lipid Membrane Interaction. Upon internalization by endocytosis, the amine groups in polycation delivery vehicles have been hypothesized to act as a "proton sponge" and increase osmotic pressure in these vesicles to help release complexes from endosomes into the cytoplasm, which may further enable nuclear transport. Therefore, the amine content per complex could play a vital role in dictating the endosomal escape efficiency. We hypothesize that compared to the charge-mediated condensation of single polycations with plasmids, the self-assembled micellar architecture allows a higher incorporation of amine groups into each micelleplex as compared to each polyplex. This physico-chemical difference could enable a higher fraction of micelleplexes escaping the endosomes compared to polyplexes, thus enabling higher transgene expression. To quantify the number of polymers and net charges in the formulations, the composition of OD polyplexes and ODB micelleplexes at N/P=5 were assessed by pulsed-field-gradient NMR (PFG-NMR) and static light scattering (SLS), respectively (FIG. 18). When one chemical species has two diffusion modes that are well separated, such as the free OD polymers ($R_h$=4.6 nm by DLS) and bound OD polymers in OD polyplexes ($R_h$=50 nm by DLS), the signal of the OD polymer follows a biexponential decay model, provided that the exchange time between the two populations is much longer than the experimental observation time. The number percentage of each population can be obtained from the fit to the biexponential model. As FIG. 18(a) shows, two diffusion modes of OD polymers were detected in OD polyplex solutions, and the percentage of bound OD polymers was calculated as 19% at N/P=5. Therefore, the bound N/P ratio of OD polyplexes, defined as the total amine groups divided by the total phosphate groups incorporated in the complexes, is 1.0. Therefore, OD polyplexes are essentially charge-neutral and co-exist with a large number of free OD polymers. This observation agrees with previous studies quantifying the compositions of similar polyplexes using 1D $^1$H NMR and analytical ultracentrifugation, respectively. Unlike OD polyplexes, the size of ODB micelles ($R_h$=34 nm) and micelleplexes ($R_h$=53 nm) are more similar, and ODB micelleplexes have a similar decay curve as ODB micelles, as shown in FIG. 19, thus separation into two modes is not reliable. Instead, the composition of ODB micelleplexes was assessed by static light scattering (SLS, FIG. 18(b)), which measured the weight-averaged molar mass ($M_{w,apparent}$) of free ODB micelles and micelleplexes. With the assumptions that all ODB micelleplexes are the same and assuming that all DNA is complexed, a range of micelleplex compositions are possible, which simultaneously satisfy $M_{w,apparent}$ and mass balance, as shown in FIG. 20. However, at N/P=5, the molar ratio of micelles to pDNA is 1.9, thus it is reasonable to assume that micelles are still the majority species in the micelleplexes. Namely, the number of micelles per micelleplex has to be greater than or equal to the number of pDNA chains per micelleplex. This assumption leads to a limit in the range of possible micelleplex compositions and suggests that at least 50% ODB micelles are incorporated in the micelleplexes and the bound N/P ratio of ODB micelleplexes is >2.5. These data reveal that micelleplexes are over-charged with excess amine groups, whereas polyplexes are not. As Table 6 summarizes, ODB micelleplexes are more highly charged with amine groups than OD polyplexes, and the direct incorporation of more amine groups could potentially enhance micelleplex endosomal escape efficiency due to the larger amine concentration per package and high buffering capacity for micelleplexes. This is potentially a major reason why micelleplexes outperform polyplexes.

TABLE 6

Compositions of OD Polyplex and ODB Micelleplex

| | OD polyplex | ODB micelleplex |
|---|---|---|
| Stoichiometric N/P | 5 | 5 |
| Fraction of polymer/micelle in complexes | $0.19^a$ | $>0.50^b$ |
| Fraction of free polymer/micelle | 0.81 | <0.50 |
| Bound N/P | $1.0^a$ | $>2.5^b$ |

Figure 21:
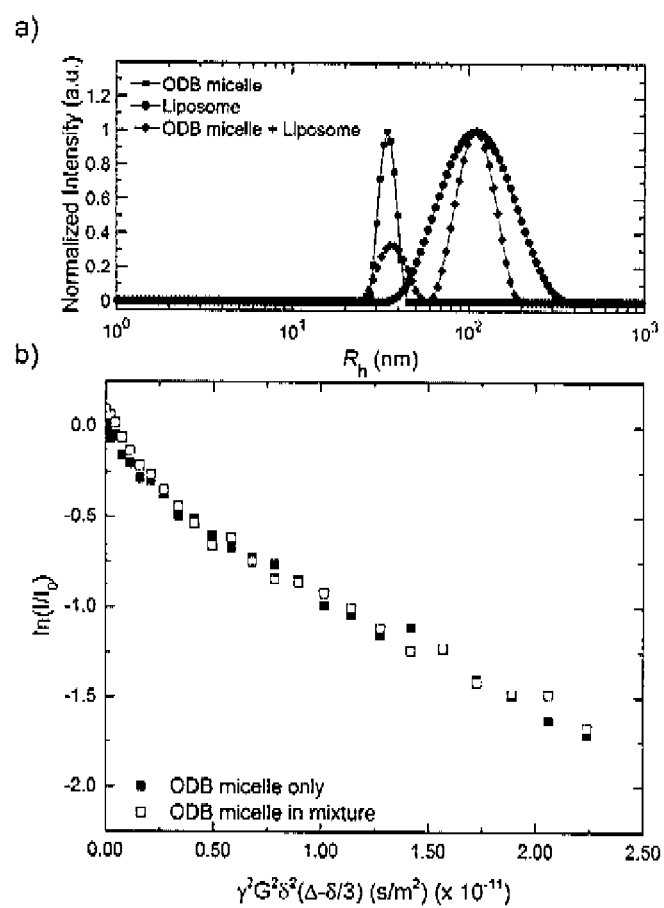
FIG. 21(a)-(b) are plots of analysis of solutions containing the micelles and liposomes (used to model potential interactions between micelles with the cell membrane).
Figure 22:
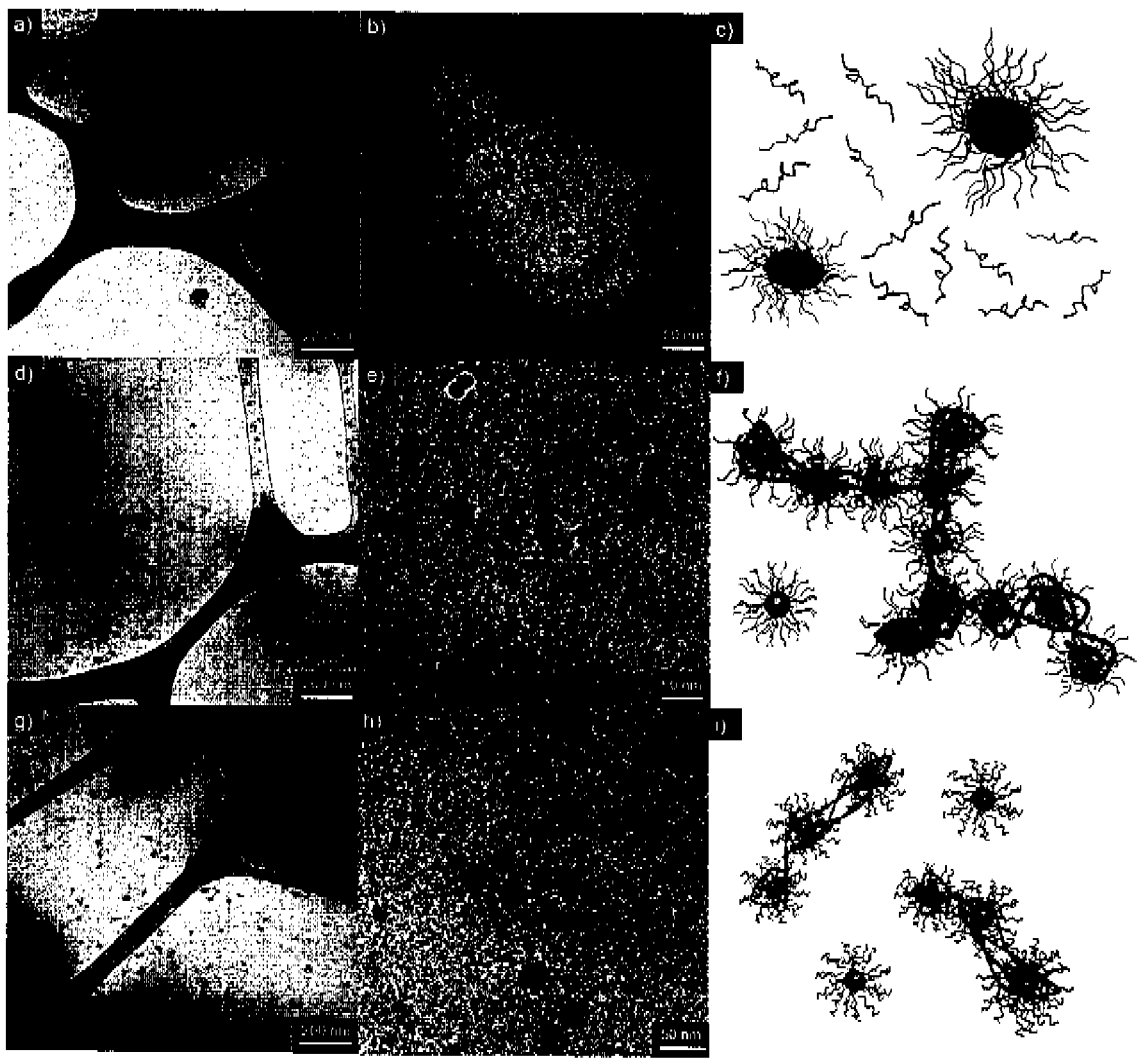
FIGS. 22(a)-(i) are cryo-TEM images of (a-b) OD polyplexes, (d-e) DB micelleplexes and (g-h) ODB micelleplexes in PBS buffer at N/P=5. Schematic illustrations of complex structures are shown for (c) OD polyplexes, (f) DB micelleplexes, and (i) ODB micelleplexes.

[a] Determined by PFG-NMR, the fitted diffusion coefficients and corresponding hydrodynamic radii are tabulated in Table S2.
[b] Estimated by SLS In additional to the "proton sponge" effect, amphiphilic molecules are known to interact with cell membranes and cellular vesicles, which could be a potential endosome disruption and escape mechanism. To assess whether the amphiphilic nature of ODB polymers/micelles aid membrane permeation/endosomal escape, the interaction between micelles and 2-oleoyl-1-palmitoyl-sn-glycero-3-phosphocholine (POPC) liposomes was assessed by dynamic light scattering (DLS) and PFG-NMR. The DLS results showed that micelles and liposomes both retain their original sizes in a micelle-liposome solution mixture (FIG. 21), which indicates that micelles neither bind to liposomes nor do they intercalate into/interact with the lipid bilayer. Moreover, the micelle diffusion coefficient remained the same both with and without the liposomes, which further suggests that there are no significant interactions between the micelles and the liposomes. This result is expected as the long hydrophobic blocks of DB and ODB polymers are embedded in micelle cores that are kinetically constrained from chain exchange and thus do not interact with liposomal (and likely cellular) membranes. Consequently, the higher transfection efficiency of the micelleplexes is likely not due to cell membrane disruption by the amphiphilicity of the DB and ODB polymers.

pDNA Packaging and Accessibility. The distinct difference in complexation architecture and stability against dissociation can also affect the overall transfection efficiency, as these collectively influence pDNA accessibility and release profiles. As revealed by cryo-TEM images shown in FIG. 22, although sharing similar cationic blocks, polyplexes and micelleplexes are considerably different in their packaging mechanism. While D polyplexes formed very large aggregates (too large to be imaged by cryo-TEM), OD polyplexes have globular shapes with complexed pDNA chains condensed in the core and hydrophilic PEG blocks surrounding the core (FIGS. 23 (a)-(c)). The encapsulation of pDNA inside polyplexes may make it less accessible for release and expression once inside the cell. In contrast, DB and ODB micelleplexes showed beads-on-a-string structures, where pDNA chains wrap around and bridge micelles (FIGS. 23 (d)-(i)), similar to DNA wrapping around histone proteins. While DB micelleplexes have a similar motif as ODB micelleplexes, the number of micelles incorporated per micelleplex is lower in the presence of the outer PEG corona. Compared to the pDNA that is condensed in the core of polyplexes, the pDNA wrapped around the micelle corona may be more accessible to transcription enzymes, and unpackaging/accessibility could be an additional primary reason for higher transgene expression. To this end, the interaction of each complex type with pDNA was further assessed via circular dichroism (CD) spectroscopy.

Figure 23:
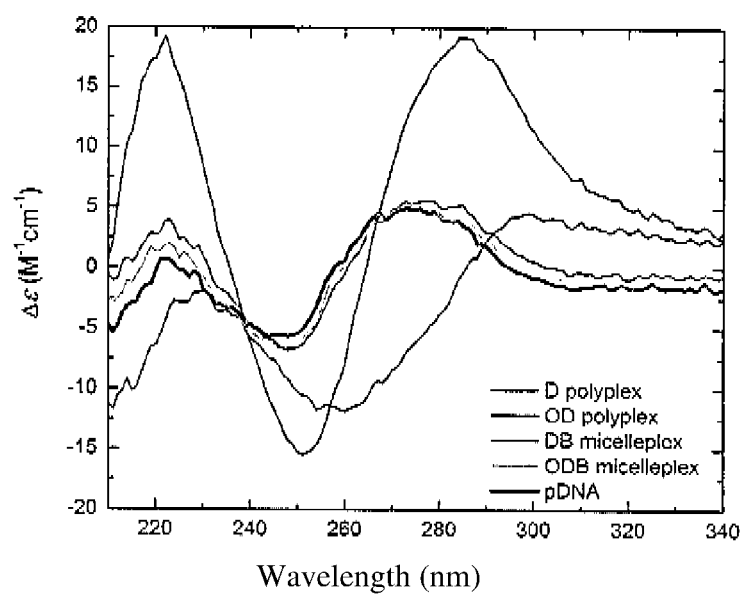
FIG. 23 is a circular dichroism spectrum of pDNA either uncomplexed (black line) or complexed in polyplexes (D: purple line; OD: blue line) and micelleplexes (DB: red line; ODB: teal line) formed in PBS buffer at pH 7.4 and 154 mM at N/P=5.
Figure 24:
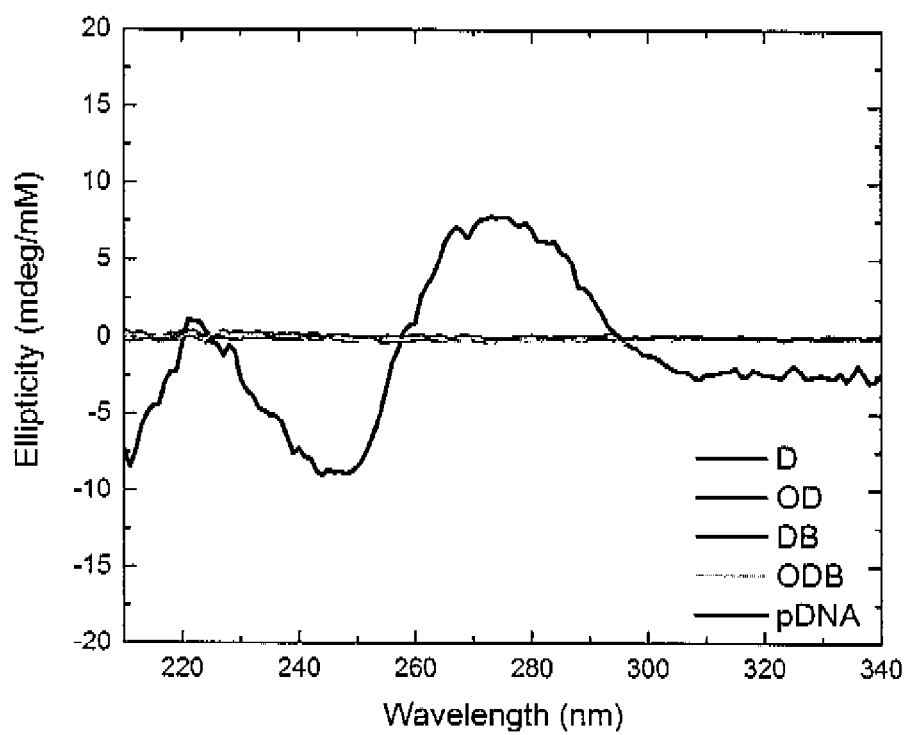
FIG. 24 is a plot of the CD signal of the uncomplexed polymers and micelles of FIG. 23.

The CD spectra shown in FIG. 23 further corroborate the differences in pDNA chain packaging between polyplexes and micelleplexes. When pDNA chains wrap around DB and ODB micelles to form micelleplexes, the helix remains intact in its native B form as shown by the lack of change in the CD signal compared to pDNA alone. However, in comparison, pDNA secondary structure is modified after being packaged in the D and OD polyplexes, as indicated by the CD signal change. In OD polyplexes, the pDNA exhibits greater helicity, as indicated by the much stronger CD signal. With the D polyplexes, a red shift in the signal was observed, which could reflect a direct interaction between polymer and pDNA bases that affect the tilt angle between base pairs and helix axis. These results suggest a much stronger binding interaction in polyplexes formed with the D and OD polymers, potentially distorting the pDNA and/or inhibiting proper accessibility of the payload to polymerase enzymes needed for effective transcription. The strong driving force for D and OD polymers to complex with pDNA compensates the energy penalty for altering DNA double helix structure. The CD spectrum of polymer solutions without pDNA showed a complete absence of ellipticity within the tested range (FIG. 24), confirming that the CD signal changes after complexation are due solely to polymer-pDNA interactions. Thus, polyplexes are likely more thermodynamically stable than micelleplexes. Collectively, in addition to the higher cellular internalization and higher density of amines in each micelleplex (could promote endosomal buffering), the optimized pDNA packaging contributes to the comparable biological efficiency.

CONCLUSION

The structure, composition, stability, and biological efficacy of polyplexes and micelleplexes are systematically compared using four polycations with the same cationic block identity and length. Polymers D and OD complex with pDNA and form polyplexes, and amphiphilic block copolymers DB and ODB self-assemble into spherical micelles and complex with pDNA to form micelleplexes. It was found that D and OD polyplexes form large aggregates or globular structures, respectively, with pDNA condensed in the core. However, micelleplexes have beads-on-a-string structures with DNA chains wrapping around and bridging among multiple polycationic micelles. Compared to polyplexes, micelleplexes exhibit more than four times higher transfection efficiency, with similar levels of cytotoxicity. Three hypotheses relating to cellular uptake, intracellular trafficking, and pDNA unpackaging were explored to pinpoint the mechanisms by which micelleplexes outperform polyplexes. It was found that micelleplexes are internalized predominantly via the same caveola-mediated pathway as polyplexes, but are internalized more efficiently. The incorporation of a higher number of amine groups per micelleplex potentially aids endosomal escape, as polyplexes have significantly lower amine numbers. In addition, the packaging of pDNA around micelles retains the native helical B form of DNA, and thus supports an amenable environment for transcription enzymes once within the cell, leading to higher protein expression, whereas polyplexes of the same cationic block significantly alter DNA helicity. The architecture of pDNA packaging and the physico-chemical properties of pDNA-vehicle complexes play direct and important roles in achieving high delivery and gene expression efficiencies. This strategy of optimizing the physical assembly properties to improve vehicle transfection efficiency (via pre-assembly of polycations into high-amine content nanoparticles) can be readily and widely applied to a broad range of polyelectrolyte complexes and payloads, including nucleic acids and proteins. These results therefore have wide-reaching potential to inform future design of polymeric vehicles for intracellular biomacromolecule delivery.

Various embodiments of the invention have been described. These and other embodiments are within the scope of the following claims.

The invention claimed is:

1. A compound, comprising:
an amphiphilic polymer, comprising:
   a hydrophobic block comprising monomeric units chosen from alkyl (meth)acrylates, alkyl (meth)acrylamides, and combinations thereof; and
   a hydrophilic cationic block comprising monomeric units chosen from alkylamino (meth)acrylates, alkylamino (meth)acrylamides, and combinations thereof; and
wherein the polymer is in the form of a micelle with a central core derived from the hydrophobic block and shell at least partially surrounding the core, wherein the shell comprises a plurality of filamentous arms derived from the hydrophilic cationic block and emanating outward from the core; and
a biological agent associated with the arms of the micelle, wherein at least one of: the hydrophobic block has a first chain length of about 1 kilodalton (kDa) to about 40 kDa, or the hydrophilic cationic block has a second chain length of about 1 kDa to about 40 kDa.

2. The compound of claim 1, wherein the micelle has a morphology chosen from spherical, rod-like, worm-like, ring-like, vesicular, and combinations thereof.

3. The compound of claim 1, wherein the micelle has a spherical morphology.

4. The compound of claim 1, wherein the first chain length of the hydrophobic block is about 1 kDa to about 40 KDa.

5. The compound of claim 1, wherein the second chain length of the hydrophilic cationic block is about 1 kDa to about 40 kDa.

6. The compound of claim 1, wherein the micelle has about 10 to about 5000 arms.

7. The compound of claim 1, wherein the amphiphilic polymer further comprises a hydrophilic nonionic block comprising ethylene glycol (PEG) monomeric units, and wherein the hydrophilic cationic block forms a first portion of the arms proximal the core and the hydrophilic nonionic block forms a second portion of the arms connected to the first portion of the arms and distal the core.

8. The compound of claim 7, wherein the hydrophilic nonionic block has a chain length of about 1 kDa to about 40 kDa.

9. The compound of claim 1, wherein the hydrophobic block comprises monomeric units of a linear or branched alkyl (meth)acrylate with about 2 to about 10 carbon atoms.

10. The compound of claim 1, wherein the hydrophilic cationic block comprises a linear alkylamino (meth)acrylate with about 2 to about 5 carbon atoms.

11. The compound of claim 7, wherein the hydrophilic nonionic block comprises poly(ethylene glycol) (PEG).

12. The compound of claim 1, wherein the biological agent is chosen from a nuclease, a nucleic acid encoding a nuclease, an oligonucleotide, a protein, a peptide, a DNA editing template, guide RNA, a therapeutic agent, a plasmid DNA encoding a protein, siRNA, mRNA, monoclonal antibodies, and mixtures and combinations thereof.

13. The compound of claim 1, wherein the biological agent is entangled within at least some of the arms of the micelle.

14. The compound of claim 1, wherein the biological agent is bound via electrostatic attraction to at least some of the arms of the micelle.

15. A composition comprising:
a pharmaceutically acceptable aqueous liquid carrier; and
a compound comprising:
   an amphiphilic polymer, comprising:
      a hydrophobic block comprising monomeric units chosen from alkyl (meth)acrylates, alkyl (meth)acrylamides, and combinations thereof; and
      a hydrophilic cationic block comprising monomeric units chosen from alkylamino (meth)acrylates, alkylamino (meth)acrylamides, and combinations thereof; and
   wherein the polymer is in the form of a micelle with a central core derived from the hydrophobic block and shell at least partially surrounding the core, wherein the shell comprises a plurality of filamentous arms derived from the hydrophilic cationic block and emanating outward from the core; and
   a biological agent associated with the arms of the micelle.

16. A composition comprising a pharmaceutically acceptable aqueous liquid carrier and a compound comprising:
an amphiphilic polymer, comprising:
   a hydrophobic block comprising monomeric units chosen from alkyl (meth)acrylates, alkyl (meth)acrylamides, and combinations thereof; and
   a hydrophilic cationic block comprising monomeric units chosen from alkylamino (meth)acrylates, alkylamino (meth)acrylamides, and combinations thereof; and
wherein the polymer is in the form of a micelle with a central core derived from the hydrophobic block and shell at least partially surrounding the core, wherein the shell comprises a plurality of filamentous arms derived from the hydrophilic cationic block and emanating outward from the core; and
a biological agent associated with the arms of the micelle, wherein the amphiphilic polymer further comprises a hydrophilic nonionic block comprising ethylene glycol (PEG) monomeric units, and wherein the hydrophilic cationic block forms a first portion of the arms proximal the core and the hydrophilic nonionic block forms a second portion of the arms connected to the first portion of the arms and distal the core.

17. A method, comprising:
applying to a cell a composition, the composition comprising:
   (a) an aqueous pharmaceutically acceptable liquid carrier;
   (b) an amphiphilic polymer, comprising:
      a hydrophobic block comprising monomeric units chosen from alkyl (meth)acrylates, alkyl (meth)acrylamides, and combinations thereof; and
      a hydrophilic cationic block comprising monomeric units chosen from alkylamino (meth)acrylates, alkylamino (meth)acrylamides, and combinations thereof; and
   wherein the copolymer is in the form of a micelle with a central core derived from the hydrophobic block and shell at least partially surrounding the core, wherein the shell comprises a plurality of filamentous arms derived from the hydrophilic cationic block and emanating outward from the core, wherein at least one of: the hydrophobic block has a first chain length of about 1 kDa to about 40 KDa, or the hydrophilic cationic block has a second chain length of about 1 kDa to about 40 kDa; and
   (c) a biological payload associated with the arms of the micelle, wherein the biological payload is delivered into the cell or tissue.

18. The method of claim 17, wherein the amphiphilic polymer further comprises a hydrophilic nonionic block comprising ethylene glycol (PEG) monomeric units, and wherein the hydrophilic cationic block forms a first portion of the arms proximal the core and the hydrophilic nonionic block forms a second portion of the arms connected to the first portion of the arms and distal the core.

19. A micelleplex comprising a plurality of amphiphilic micelles, wherein at least a portion of the amphiphilic micelles are bonded to a biological agent, the amphiphilic micelles each comprising:
a hydrophobic block comprising monomeric units chosen from alkyl (meth)acrylates, alkyl (meth)acrylamides, and combinations thereof;
a hydrophilic cationic block comprising monomeric units chosen from alkylamino (meth)acrylates, alkylamino (meth)acrylamides, and combinations thereof; and
wherein each amphiphilic micelle comprises a central core derived from the hydrophobic block, and shell at least partially surrounding the core, and wherein the shell comprises a plurality of filamentous arms derived from the hydrophilic cationic block and emanating outward from the core, wherein at least one of: the hydrophobic block has a first chain length of about 1 kDa to about 40 KDa, or the hydrophilic cationic block has a second chain length of about 1 kDa to about 40 kDa.

20. The micelleplex of claim 19, wherein the amphiphilic polymer in at least a portion of the amphiphilic micelles further comprises a hydrophilic nonionic block comprising ethylene glycol (PEG) monomeric units, and wherein the hydrophilic cationic block forms a first portion of the arms proximal the core and the hydrophilic nonionic block forms a second portion of the arms connected to the first portion of the arms and distal the core.

21. The micelleplex of claim 19, wherein the amphiphilic micelles are in an aqueous solution.

22. The micelleplex of claim 21, wherein the aqueous solution is a pharmaceutically acceptable liquid carrier.

23. The method of claim 17, wherein the micelle has a spherical morphology.

24. The method of claim 19, wherein each amphiphilic micelle has a spherical morphology.

\* \* \* \* \*